(12) United States Patent
Bullington et al.

(10) Patent No.: US 9,788,774 B2
(45) Date of Patent: Oct. 17, 2017

(54) METHODS AND APPARATUS FOR SELECTIVELY OCCLUDING THE LUMEN OF A NEEDLE

(71) Applicant: Magnolia Medical Technologies, Inc., Seattle, WA (US)

(72) Inventors: Gregory Bullington, Bellevue, WA (US); Richard G. Patton, Seattle, WA (US); Jay M. Miazga, Seattle, WA (US); Shan E. Gaw, Seattle, WA (US)

(73) Assignee: Magnolia Medical Technologies, Inc., Seattle, WA (US)

( * ) Notice: Subject to any disclaimer, the term of this patent is extended or adjusted under 35 U.S.C. 154(b) by 0 days.

(21) Appl. No.: 14/490,099

(22) Filed: Sep. 18, 2014

(65) Prior Publication Data

US 2015/0250414 A1  Sep. 10, 2015

Related U.S. Application Data

(63) Continuation of application No. 14/200,453, filed on Mar. 7, 2014.
(Continued)

(51) Int. Cl.
*A61B 5/15* (2006.01)
*A61M 5/158* (2006.01)
(Continued)

(52) U.S. Cl.
CPC ....... *A61B 5/150633* (2013.01); *A61M 5/158* (2013.01); *A61M 5/16804* (2013.01);
(Continued)

(58) Field of Classification Search
CPC .......... A61M 5/158; A61M 2005/1585; A61M 2005/1587; A61M 2205/0266;
(Continued)

(56) References Cited

U.S. PATENT DOCUMENTS 2,707,953 A   5/1955  Ryan
2,847,995 A   8/1958  Adams
(Continued)

FOREIGN PATENT DOCUMENTS

EP   0608985 B1   2/1997
EP   0761173 A2   3/1997
(Continued)

OTHER PUBLICATIONS

International Search Report and Written Opinion mailed Jun. 25, 2014, issued for International Patent Application No. PCT/US2014/021564 (13 pages).
(Continued)

*Primary Examiner* — Kevin C Sirmons
*Assistant Examiner* — Amber Stiles
(74) *Attorney, Agent, or Firm* — Cooley LLP

(57) ABSTRACT

A fluid transfer device for parenterally transferring fluid to and/or from a patient includes a housing, a needle, and an occlusion mechanism. The housing defines a fluid flow path and is couplable to a fluid reservoir. The needle has a distal end portion that is configured to be inserted into the patient and a proximal end portion that is configured to be fluidically coupled to the fluid flow path of the housing, and defines a lumen therebetween. The occlusion mechanism selectively controls a fluid flow between the needle and the fluid flow path. The occlusion mechanism includes an occlusion member that is movable between a first configuration where the lumen of the needle is obstructed during insertion into the patient and a second configuration where the lumen of the needle is unobstructed after the needle has been inserted into the patient allowing fluid transfer to or from the patient.

5 Claims, 27 Drawing Sheets

Related U.S. Application Data

(60) Provisional application No. 61/777,758, filed on Mar. 12, 2013.

(51) Int. Cl.
*A61M 39/22* (2006.01)
*A61M 5/168* (2006.01)
*A61M 5/32* (2006.01)

(52) U.S. Cl.
CPC ............ *A61M 39/22* (2013.01); *A61M 5/3291* (2013.01); *A61M 2005/1585* (2013.01); *A61M 2005/1587* (2013.01); *A61M 2205/0205* (2013.01); *A61M 2205/0238* (2013.01); *A61M 2205/0266* (2013.01)

(58) Field of Classification Search
CPC ............ A61M 25/007; A61M 25/0074; A61M 25/0075; A61M 25/06; A61M 25/0606; A61M 25/065; A61M 2025/0004; A61M 2025/0079; A61M 2025/0656; A61M 5/16804; A61M 39/22; A61M 2205/0205; A61M 5/3291; A61M 2205/0238; A61B 5/150633
USPC .............. 604/93.01, 164.01, 164.02, 164.03, 604/164.06, 164.12, 166.01, 167.01, 604/167.06, 264, 272, 274; 600/567
See application file for complete search history.

(56) References Cited

U.S. PATENT DOCUMENTS

| | | | |
|---|---|---|---|
| 2,850,007 A | 9/1958 | Lingley | |
| 2,992,974 A | 7/1961 | Belcove et al. | |
| 3,013,557 A | 12/1961 | Pallotta | |
| 3,098,016 A | 7/1963 | Cooper et al. | |
| 3,304,934 A | 2/1967 | Bautista | |
| 3,382,865 A | 5/1968 | Worral, Jr. | |
| 3,405,706 A | 10/1968 | Cinqualbre | |
| 3,494,351 A | 2/1970 | Horn | |
| 3,577,980 A | 5/1971 | Cohen | |
| 3,635,798 A | 1/1972 | Kirkham et al. | |
| 3,648,684 A | 3/1972 | Barnwell et al. | |
| 3,777,773 A | 12/1973 | Tolbert | |
| 3,848,579 A | 11/1974 | Villa-Real | |
| 3,848,581 A | 11/1974 | Cinqualbre et al. | |
| 3,890,203 A | 6/1975 | Mehl | |
| 3,890,968 A | 6/1975 | Pierce et al. | |
| 3,937,211 A | 2/1976 | Merten | |
| 4,057,050 A | 11/1977 | Sarstedt | |
| 4,063,460 A | 12/1977 | Svensson | |
| 4,133,863 A | 1/1979 | Koenig | |
| 4,166,450 A | 9/1979 | Abramson | |
| 4,340,067 A | 7/1982 | Rattenborg | |
| 4,370,987 A | 2/1983 | Bazell et al. | |
| 4,416,291 A | 11/1983 | Kaufman | |
| 4,425,235 A | 1/1984 | Cornell et al. | |
| 4,444,203 A | 4/1984 | Engelman | |
| 4,459,997 A | 7/1984 | Sarstedt | |
| 4,509,534 A | 4/1985 | Tassin, Jr. | |
| 4,537,593 A | 8/1985 | Alchas | |
| 4,657,160 A | 4/1987 | Woods et al. | |
| 4,673,386 A | 6/1987 | Gordon | |
| 4,676,256 A | 6/1987 | Golden | |
| 4,737,146 A | 4/1988 | Amaki et al. | |
| 4,790,830 A | 12/1988 | Hamacher | |
| 4,808,157 A | 2/1989 | Coombs | |
| 4,865,583 A | 9/1989 | Tu | |
| 4,890,627 A | 1/1990 | Haber et al. | |
| 4,976,697 A * | 12/1990 | Walder ............... | A61M 25/0113 604/164.02 |
| 4,988,339 A | 1/1991 | Vadher | |
| 5,009,847 A | 4/1991 | Solomons | |
| 5,064,411 A * | 11/1991 | Gordon, III ................ | 604/48 |
| 5,097,842 A | 3/1992 | Bonn | |
| 5,100,390 A | 3/1992 | Lubeck et al. | |
| 5,108,927 A | 4/1992 | Dom | |
| 5,122,129 A | 6/1992 | Olson et al. | |
| 5,234,406 A | 8/1993 | Drasner et al. | |
| 5,269,317 A | 12/1993 | Bennett | |
| 5,312,345 A | 5/1994 | Cole | |
| 5,330,464 A | 7/1994 | Mathias et al. | |
| 5,360,011 A | 11/1994 | McCallister | |
| 5,423,824 A | 6/1995 | Akerfeldt | |
| 5,429,610 A | 7/1995 | Vaillancourt | |
| 5,431,635 A | 7/1995 | Yoon | |
| 5,449,351 A | 9/1995 | Zohmann | |
| 5,450,856 A | 9/1995 | Norris | |
| 5,454,786 A | 10/1995 | Harris | |
| 5,485,854 A | 1/1996 | Hollister | |
| 5,507,299 A | 4/1996 | Roland | |
| 5,511,556 A * | 4/1996 | DeSantis ............ | A61B 10/0283 600/562 |
| 5,573,510 A | 11/1996 | Isaacson | |
| 5,577,513 A | 11/1996 | Van Vlassalaer | |
| 5,578,053 A * | 11/1996 | Yoon ............... | A61B 10/0233 606/165 |
| 5,628,734 A | 5/1997 | Hatfalvi | |
| 5,718,678 A | 2/1998 | Fleming, III | |
| 5,762,633 A | 6/1998 | Whisson | |
| 5,807,338 A | 9/1998 | Smith et al. | |
| 5,823,970 A * | 10/1998 | Terwilliger ............... | 600/564 |
| 5,848,996 A | 12/1998 | Eldor | |
| 5,865,812 A | 2/1999 | Correia | |
| 5,882,318 A | 3/1999 | Boyde | |
| 5,922,551 A | 7/1999 | Durbin et al. | |
| 6,016,712 A | 1/2000 | Warden et al. | |
| 6,020,196 A | 2/2000 | Hu et al. | |
| 6,024,725 A | 2/2000 | Bollinger et al. | |
| 6,057,105 A | 5/2000 | Hoon et al. | |
| 6,159,164 A | 12/2000 | Neese et al. | |
| 6,210,909 B1 | 4/2001 | Guirguis | |
| 6,328,726 B1 | 12/2001 | Ishida et al. | |
| 6,364,890 B1 | 4/2002 | Lum et al. | |
| 6,387,086 B2 | 5/2002 | Mathias et al. | |
| 6,403,381 B1 | 6/2002 | Mann et al. | |
| 6,478,775 B1 | 11/2002 | Galt et al. | |
| 6,520,948 B1 | 2/2003 | Mathias et al. | |
| 6,554,809 B2 | 4/2003 | Aves | |
| 6,626,884 B1 | 9/2003 | Dillon et al. | |
| 6,692,479 B2 | 2/2004 | Kraus et al. | |
| 6,716,187 B1 | 4/2004 | Jorgensen et al. | |
| 6,746,420 B1 | 6/2004 | Prestidge et al. | |
| 6,913,580 B2 | 7/2005 | Stone | |
| 7,025,751 B2 | 4/2006 | Silva et al. | |
| 7,044,941 B2 | 5/2006 | Mathias et al. | |
| 7,060,060 B1 | 6/2006 | Simpson et al. | |
| 7,087,047 B2 | 8/2006 | Kraus et al. | |
| 7,204,828 B2 | 4/2007 | Rosiello | |
| 7,211,074 B2 | 5/2007 | Sansoucy | |
| 7,258,694 B1 | 8/2007 | Choi et al. | |
| 7,335,188 B2 | 2/2008 | Graf | |
| 7,384,416 B2 | 6/2008 | Goudaliez et al. | |
| 7,744,573 B2 | 6/2010 | Gordon et al. | |
| 7,993,310 B2 | 8/2011 | Rosiello | |
| 8,197,420 B2 | 6/2012 | Patton | |
| 8,231,546 B2 | 7/2012 | Patton | |
| 8,292,841 B2 | 10/2012 | Gregersen | |
| 8,337,418 B2 | 12/2012 | Patton | |
| 8,535,241 B2 | 9/2013 | Bullington et al. | |
| 8,647,286 B2 | 2/2014 | Patton | |
| 8,864,684 B2 | 10/2014 | Bullington et al. | |
| 8,876,734 B2 | 11/2014 | Patton | |
| 9,022,950 B2 | 5/2015 | Bullington et al. | |
| 9,022,951 B2 | 5/2015 | Bullington et al. | |
| 9,060,724 B2 | 6/2015 | Bullington et al. | |
| 9,060,725 B2 | 6/2015 | Bullington et al. | |
| 9,283,331 B2 | 3/2016 | Olson | |
| 2002/0002349 A1 | 1/2002 | Flaherty et al. | |
| 2002/0042581 A1 | 4/2002 | Cervi | |
| 2002/0072720 A1* | 6/2002 | Hague et al. ................ | 604/264 |
| 2002/0107469 A1 | 8/2002 | Bolan et al. | |

(56) References Cited

U.S. PATENT DOCUMENTS

| | | |
|---|---|---|
| 2002/0183651 A1 | 12/2002 | Hyun |
| 2002/0193751 A1 | 12/2002 | Theeuwes et al. |
| 2003/0055381 A1 | 3/2003 | Wilkinson |
| 2003/0069543 A1 | 4/2003 | Carpenter et al. |
| 2003/0139752 A1 | 7/2003 | Pasricha et al. |
| 2003/0208151 A1 | 11/2003 | Kraus et al. |
| 2003/0225344 A1 | 12/2003 | Miller |
| 2004/0010228 A1 | 1/2004 | Swenson et al. |
| 2004/0054283 A1 | 3/2004 | Corey et al. |
| 2004/0054333 A1 | 3/2004 | Theeuwes et al. |
| 2004/0147855 A1 | 7/2004 | Marsden |
| 2004/0167427 A1 | 8/2004 | Quick et al. |
| 2005/0004524 A1 | 1/2005 | Newby et al. |
| 2005/0131344 A1 | 6/2005 | Godaire |
| 2005/0148993 A1 | 7/2005 | Mathias et al. |
| 2005/0240161 A1 | 10/2005 | Crawford |
| 2005/0245885 A1 | 11/2005 | Brown |
| 2005/0281713 A1 | 12/2005 | Hampsch et al. |
| 2006/0287639 A1 | 12/2006 | Sharp |
| 2007/0100250 A1 | 5/2007 | Kline |
| 2008/0108954 A1 | 5/2008 | Mathias et al. |
| 2008/0145933 A1 | 6/2008 | Patton |
| 2009/0306601 A1 | 12/2009 | Shaw et al. |
| 2010/0152681 A1 | 6/2010 | Mathias |
| 2010/0234760 A1* | 9/2010 | Almazan ............ A61B 10/0275 600/566 |
| 2012/0035540 A1 | 2/2012 | Ferren et al. |
| 2012/0083740 A1 | 4/2012 | Chebator et al. |
| 2012/0095367 A1 | 4/2012 | Patton |
| 2012/0215131 A1 | 8/2012 | Patton |
| 2013/0079604 A1 | 3/2013 | Patton |
| 2013/0116599 A1 | 5/2013 | Bullington et al. |
| 2014/0039348 A1 | 2/2014 | Bullington et al. |
| 2014/0107564 A1 | 4/2014 | Bullington et al. |
| 2014/0155781 A1 | 6/2014 | Bullington et al. |
| 2014/0155782 A1 | 6/2014 | Bullington et al. |
| 2014/0163419 A1 | 6/2014 | Bullington et al. |
| 2014/0276578 A1 | 9/2014 | Bullington et al. |
| 2015/0018715 A1 | 1/2015 | Walterspiel |
| 2015/0032067 A1 | 1/2015 | Bullington et al. |
| 2015/0073348 A1 | 3/2015 | Bullington et al. |
| 2015/0094615 A1 | 4/2015 | Patton |

FOREIGN PATENT DOCUMENTS

| | | |
|---|---|---|
| EP | 0727187 B1 | 6/2003 |
| WO | WO 2005/068011 | 7/2005 |
| WO | WO 2008/077047 | 6/2008 |
| WO | WO 2013/181352 | 12/2013 |
| WO | WO 2014/022275 | 2/2014 |
| WO | WO 2014/058945 | 4/2014 |
| WO | WO 2014/085800 | 6/2014 |
| WO | WO 2014/089186 | 6/2014 |
| WO | WO 2014/099266 | 6/2014 |
| WO | WO 2014/164263 | 10/2014 |

OTHER PUBLICATIONS

Medical Surgical Systems Catalogue (Canadian Version), BD Medical, 2010, 51 pages.

International Search Report and Written Opinion for International Application No. PCT/US2007/087951 mailed May 16, 2008, 8 pages.

Office Action for U.S. Appl. No. 11/955,635, mailed Jul. 22, 2010, 11 pages.

Office Action for U.S. Appl. No. 11/955,635, mailed Dec. 3, 2010, 11 pages.

Office Action for U.S. Appl. No. 13/335,241, mailed Apr. 20, 2012, 12 pages.

Office Action for U.S. Appl. No. 13/458,508, mailed Jul. 24, 2012, 13 pages.

Office Action for U.S. Appl. No. 13/675,295, mailed May 23, 2013, 15 pages.

Office Action for U.S. Appl. No. 14/089,267, mailed Jun. 19, 2014, 13 pages.

Office Action for U.S. Appl. No. 13/954,528, mailed Mar. 17, 2014, 10 pages.

International Search Report and Written Opinion for International Application No. PCT/US2013/071491, mailed Aug. 5, 2014, 9 pages.

International Search Report and Written Opinion for International Application No. PCT/US2013/043289, mailed Oct. 24, 2013, 15 pages.

Office Action for U.S. Appl. No. 14/493,796, mailed Jan. 27, 2015, 7 pages.

Office Action for U.S. Appl. No. 14/494,208, mailed Jan. 27, 2015, 7 pages.

International Search Report and Written Opinion for International Application No. PCT/US2013/073080, mailed Feb. 18, 2014, 14 pages.

International Search Report and Written Opinion for International Application No. PCT/US2013/063975, mailed Mar. 20, 2014, 16 pages.

Office Action for U.S. Appl. No. 14/049,326, mailed Apr. 24, 2015, 10 pages.

International Search Report and Written Opinion for International Application No. PCT/US2013/052493, mailed Nov. 27, 2013, 7 pages.

Office Action for U.S. Appl. No. 13/952,964, mailed Mar. 20, 2015, 11 pages.

Arkin, C. F. et al., "Procedures for the Collection of Diagnostic Blood Specimens by Venipuncture; Approved Standard," Fifth Edition, Clinical and Laboratory Standards Institute, vol. 23, No. 32 (2003), 52 pages.

Calam, R. R., "Recommended 'Order of Draw' for Collecting Blood Specimens Into Additive-Containing Tubes," Letter to the Editor, Clinical Chemistry, 28(6):1399 (1982).

Hall, K. K. et al., "Updated Review of Blood Culture Contamination," Clinical Microbiology Reviews, 19(4):788-802 (2006).

Kim, J. Y. et al., "The Sum of the Parts is Greater Than the Whole: Reducing Blood Culture Contamination," Annals of Internal Medicine, 154:202-203 (2011).

Levin, P. D. et al., "Use of the Nonwire Central Line Hub to Reduce Blood Culture Contamination," Chest, 143(3):640-645 (2013).

Order of Draw for Multiple Tube Collections, LabNotes, a newsletter from BD Diagnostics,—Preanalytical Systems, 17(1):3 (2007).

Patton, R. G. et al., "Innovation for Reducing Blood Culture Contamination: Initial Specimen Diversion Technique," Journal of Clinical Microbiology, 48(12):4501-4503 (2010).

Proehl, J. A. et al., "Clinical Practice Guideline: Prevention of Blood Culture Contamination, Full Version," 2012 ENA Emergency Nurses Resources Development Committee, Emergency Nurses Association (Dec. 2012), 14 pages.

Schuur, J., "Blood Cultures: When Do they Help and When Do They Harm?" Brigham & Women's Hospital, Department of Emergency Medicine, (Jun. 21-23, 2012), 42 pages.

Sibley, C. D. et al., "Molecular Methods for Pathogen and Microbial Community Detection and Characterization: Current and Potential Application in Diagnostic Microbiology," Infection, Genetics and Evolution 12:505-521 (2012).

Stohl, S. et al., "Blood Cultures at Central Line Insertion in the Intensive Care Unit: Comparison with Peripheral Venipuncture," Journal of Clinical Microbiology, 49(7):2398-2403 (2011).

Wagner et al., "Diversion of Initial Blood Flow to Prevent Whole-Blood Contamination by Skin Surface Bacteria: an in vitro model," Transfusion, 40:335-338 (2000).

Wang, P. et al., "Strategies on Reducing Blood Culture Contamination," Reviews in Medical Microbiology, 23:63-66 (2012).

Office Action for U.S. Appl. No. 14/496,296, mailed Jun. 25, 2015, 34 pages.

Office Action for U.S. Appl. No. 14/200,453, mailed Feb. 29, 2016, 15 pages.

Office Action for U.S. Appl. No. 14/496,296, mailed Jan. 15, 2016, 26 pages.

(56) References Cited

OTHER PUBLICATIONS

Office Action for U.S. Appl. No. 14/496,296, mailed Sep. 30, 2016, 19 pages.
Office Action for U.S. Appl. No. 14/200,453, mailed Nov. 8, 2016, 21 pages.

* cited by examiner

METHODS AND APPARATUS FOR SELECTIVELY OCCLUDING THE LUMEN OF A NEEDLE

CROSS-REFERENCE TO RELATED APPLICATIONS

This application is a continuation of U.S. patent application Ser. No. 14/200,453, filed Mar. 7, 2014, entitled "Methods and Apparatus for Selectively Occluding the Lumen of a Needle," which claims priority to and the benefit of U.S. Provisional Patent Application Ser. No. 61/777,758 entitled, "Lumenless Needle for Bodily Fluid Sample Collection," filed Mar. 12, 2013, the disclosures of which are incorporated herein by reference in their entirety.

BACKGROUND

Embodiments described herein relate generally to transferring fluid to or from a patient, and more particularly to devices and methods for transferring fluid to or from a patient with reduced contamination from microbes or other contaminants exterior to the body and/or the fluid source, such as dermally residing microbes.

Human skin is normally habituated in variable small amounts by certain bacteria such as coagulase-negative *Staphylococcus* species, *Proprionobacterium acnes*, *Micrococcus* species, *Streptococci Viridans* group, *Corynebacterium* species, and *Bacillus* species. These bacteria for the most part live in a symbiotic relationship with human skin but in some circumstances can give rise to serious infections in the blood stream known as septicemia. Septicemia due to these skin residing organisms is most often associated with an internal nidus of bacterial growth at the site of injured tissue, for example a damaged, scarred heart valve, or a foreign body (often an artificial joint, vessel, or valve). Furthermore, there are predisposing factors to these infections such as malignancy, immunosuppression, diabetes mellitus, obesity, rheumatoid arthritis, psoriasis, and advanced age. In some instances, these infections can cause serious illness and/or death. Moreover, these infections can be very expensive and difficult to treat and often can be associated with medical related legal issues.

In general medical practice, blood is drawn from veins (phlebotomy) for two main purposes; (1) donor blood in volumes of approximately 500 ml is obtained for the treatment of anemia, deficient blood clotting factors including platelets and other medical conditions; and (2) smaller volumes (e.g., from a few drops to 10 mL or more) of blood are obtained for testing purposes. In each case, whether for donor or testing specimens, a fluid communicator (e.g., catheter, cannula, needle, etc.) is used to penetrate and enter a vein (known as venipuncture) enabling the withdrawal of blood into a tube or vessel apparatus in the desired amounts for handling, transport, storage and/or other purposes. The site of venipuncture, most commonly the antecubital fossa, is prepared by cleansing with antiseptics to prevent the growth of skin residing bacteria in blood withdrawn from the vein. It has been shown that venipuncture needles dislodge fragments of skin including hair and sweat gland structures as well as subcutaneous fat and other adnexal structures not completely sterilized by skin surface antisepsis. These skin fragments can cause septicemia in recipients of donor blood products, false positive blood culture tests, and other undesirable outcomes. Furthermore, methods, procedures and devices are in use, which divert the initial portion of venipuncture blood enabling exclusion of these skin fragments from the venipuncture specimen in order to prevent septicemia in recipients of donor blood products, false positive blood culture tests and other undesirable outcomes.

Venipuncture is also the most common method of accessing the blood stream of a patient to deliver parenteral fluids into the blood stream of patients needing this type of medical treatment. Fluids in containers are allowed to flow into the patient's blood stream through tubing connected to the venipuncture needle or through a catheter that is placed into a patient's vasculature (e.g. peripheral IV, central line, etc.). During this process, fragments of incompletely sterilized skin with viable skin residing microbes can be delivered into the blood stream with the flow of parenteral fluids and/or at the time of venipuncture for introduction and insertion of a peripheral catheter. These fragments are undesirable in the blood stream and their introduction into the blood stream of patients (whether due to dislodging of fragments by venipuncture needle when inserting a catheter or delivered through tubing attached to needle or catheter) is contrary to common practices of antisepsis. Further, these skin fragments with viable microbes can be associated with a well-known phenomenon of colonization by skin residing organisms of the luminal surface of tubing and tubing connectors utilized to deliver parenteral fluids. The colonization is not typically indicative of a true infection but can give rise to false positive blood culture tests, which may result in antibiotic treatment, laboratory tests, and replacement of the tubing apparatus with attendant patient risks and expenses all of which are unnecessary. Furthermore, the risk of clinically significant serious infection due to skin residing organisms is increased.

As such, a need exists for improved fluid transfer devices, catheter introduction techniques and devices, as well as methods for transferring fluid to or from a patient with reduced microbial contamination and inadvertent injection of undesirable external microbes into a patient's blood stream.

SUMMARY

Devices and methods for delivering a fluid to a patient and/or introducing a peripheral catheter with reduced contamination from dermally residing microbes or other contaminants exterior to the body are described herein. In some embodiments, a fluid transfer device for parenterally transferring fluid to and/or from a patient includes a housing, a needle, and an occlusion mechanism. The housing defines a fluid flow path and is couplable to a fluid reservoir. The needle has a distal end portion that is configured to be inserted into the patient and a proximal end portion that is configured to be fluidically coupled to the fluid flow path of the housing. The needle defines a lumen between the proximal end portion and the distal end portion. The occlusion mechanism is operable to selectively control a fluid flow between the needle and the fluid flow path. The occlusion mechanism includes an occlusion member that is movable between a first configuration where the lumen of the needle is obstructed during insertion into the patient and a second configuration where the lumen of the needle is unobstructed after the needle has been inserted into the patient allowing fluid transfer to or from the patient.

DETAILED DESCRIPTION

Figure 1:
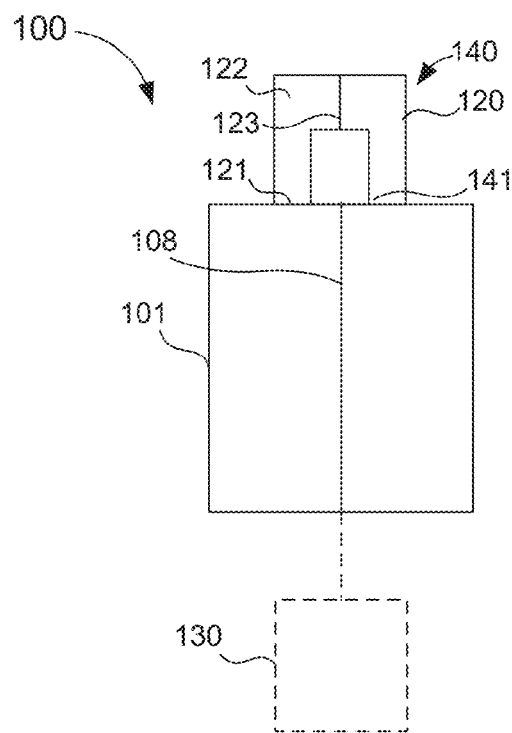
FIGS. 1 and 2 are schematic illustrations of a fluid transfer device in a first configuration and a second configuration, respectively, according to an embodiment.

In some embodiments, a fluid transfer device for parenterally transferring fluid to and/or from a patient includes a housing, a needle, and an occlusion mechanism. The housing defines a fluid flow path and is coupleable to a fluid reservoir. The needle has a distal end portion that is configured to be inserted into the patient and a proximal end portion that is configured to be fluidically coupled to the fluid flow path of the housing. The needle defines a lumen between the proximal end portion and the distal end portion. The occlusion mechanism is operable to selectively control a fluid flow between the needle and the fluid flow path. The occlusion mechanism includes an occlusion member that is movable between a first configuration where the lumen of the needle is obstructed during insertion into the patient and a second configuration where the lumen of the needle is unobstructed after the needle has been inserted into the patient allowing fluid transfer to or from the patient.

In some embodiments, a fluid transfer device for parenterally transferring fluid to and/or from a patient includes a needle and an occlusion mechanism. The needle has a proximal end portion that is configured to be fluidically coupled to a fluid reservoir and a distal end portion that is configured to be inserted into the patient. The needle defines a lumen between the proximal end portion and the distal end portion. The occlusion mechanism is operable to selectively control a fluid flow between the patient and the fluid reservoir. The occlusion mechanism has a first configuration where the lumen of the needle is obstructed during insertion into the patient and a second configuration where the lumen of the needle is unobstructed after the needle has been inserted into the patient allowing fluid transfer to or from the patient. The occlusion mechanism is configured to automatically transition from the first configuration to the second configuration when the distal end portion of the needle is inserted into the patient.

In some embodiments, a method for transferring a fluid to or from a patient uses a parenteral transfer device that has a needle and an occlusion mechanism. The needle defines a lumen and is configured to be inserted into the patient. The occlusion mechanism is operable to selectively control fluid flow to or from the patient through the lumen of the needle. The method includes disposing the occlusion mechanism in a first configuration in which the lumen of the needle is obstructed to prevent tissue, bodily fluid, and contaminants from entering the lumen. The method includes inserting the needle into the patient and, after the needle has been inserted into the patient, moving the occlusion mechanism to a second configuration in which the lumen of the needle is unobstructed to allow fluid transfer to or from the patient.

As referred to herein, "bodily fluid" can include any fluid obtained from a body of a patient, including, but not limited to, blood, cerebrospinal fluid, urine, bile, lymph, saliva, synovial fluid, serous fluid, pleural fluid, amniotic fluid, and the like, or any combination thereof.

As used herein, the term "set" can refer to multiple features or a singular feature with multiple parts. For example, when referring to set of walls, the set of walls can be considered as one wall with distinct portions, or the set of walls can be considered as multiple walls. Similarly stated, a monolithically constructed item can include a set of walls. Such a set of walls can include, for example, multiple portions that are in discontinuous from each other. A set of walls can also be fabricated from multiple items that are produced separately and are later joined together (e.g., via a weld, an adhesive or any suitable method).

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

Figure 2:
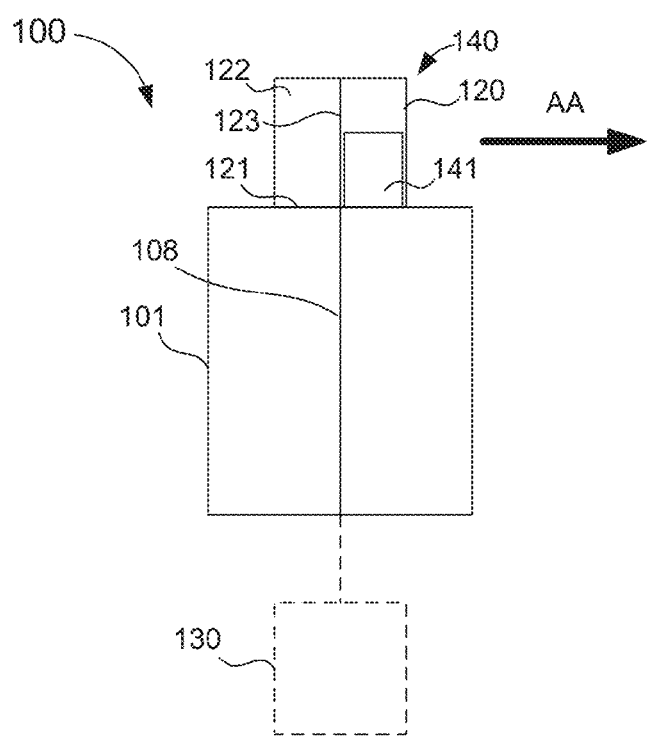

FIGS. 1 and 2 are schematic illustrations of a fluid transfer device 100 according to an embodiment, in a first and second configuration, respectively. Generally, the fluid transfer device 100 (also referred to herein as "transfer device") configured to facilitate the insertion of a piercing member (e.g., a needle, a trocar, a cannula, or the like) into a patient and to transfer a fluid to or from the patient with reduced contamination from, for example, dermally residing microbes by selectively obstructing a lumen of piercing member.

As shown in FIG. 1, the transfer device 100 includes a housing 101, a needle 120, and an occlusion mechanism 140. As described in further detail herein, the transfer device 100 can be coupled to a fluid reservoir 130 that can receive a flow of fluid from the transfer device 100 and/or transfer a flow of fluid to the transfer device 100. The housing 101 can be any suitable shape, size, or configuration and is described in further detail herein with respect to specific embodiments. As shown in FIG. 1, a portion of the housing 101 can be, at least temporarily, physically and fluidically coupled to the needle 120. For example, in some embodiments, a distal end portion of the housing 101 can include a port (not shown in FIGS. 1 and 2) configured to physically and fluidically couple to a lock mechanism (not shown in FIGS. 1 and 2) included in the needle 120. In such embodiments, the lock mechanism can be, for example, a Luer-Lok® or the like that can engage the port. In some embodiments, the housing 101 can be monolithically formed with at least a portion of the needle 120. In this manner, a portion of the housing 101 can receive a bodily fluid from and/or deliver a parenteral fluid to a patient via a lumen 123 defined by the needle 120, as described in further detail herein.

Similarly, the housing 101 is fluidically coupled to the fluid reservoir 130. In some embodiments, the proximal end portion of the housing 101 can include a port or lock mechanism (e.g., a Luer-Lok®) that can engage a portion of the fluid reservoir 130 to physically and fluidically couple the housing 101 to the fluid reservoir 130. In other embodiments, the housing 101 can be coupled to intervening structure such as, for example, a cannula that is configured to fluidically couple the housing 101 to the fluid reservoir 130. While shown in FIGS. 1 and 2 as being disposed outside of the housing 101, in some embodiments, the fluid reservoir 130 can be disposed substantially inside the housing 101 (e.g., at least a portion of the housing 101 can define the fluid reservoir 130). In this manner, the housing 101 can be configured to define a fluid flow path 108 between the needle 120 and the fluid reservoir 130, as described in further detail herein. The fluid reservoir 130 can be any suitable reservoir such as, for example, those described in U.S. Pat. No. 8,197,420 ("the '420 Patent"), entitled, "Systems and Methods for Parenterally Procuring Bodily-Fluid Samples with Reduced Contamination," filed on Dec. 13, 2007, the disclosure of which is incorporated herein by reference in its entirety. In some embodiments, the fluid reservoir can be similar to known fluid reservoirs such as, for example, a BacT/ALERT® SN or a BacT/ALERT® FA, manufactured by BIOMERIEUX, INC. and/or a standard Vacutainer® or a Microtainer® manufactured by Becton Dickinson. In this manner, the external fluid reservoir can be configured such that a negative, or sub-atmospheric, pressure exists within an inner volume of the reservoir. In other embodiments, the fluid reservoir, 130, can contain fluids (e.g. saline solution, medications, etc.) intended for delivery to the patient. In still other embodiments, the fluid reservoir 130 can be any suitable reservoir, vial, microvial, microliter vial, container, microcontainer, nanoviral (e.g., a Nanotainer™ manufactured by Thermos), or the like. In some embodiments, the fluid reservoir 130 can be any suitable sample or culture bottle such as, for example, aerobic culture bottles, anaerobic culture bottles, and or the like that can include a culture medium or the like. In this manner, the culture bottle can receive a bodily-fluid sample, which can then be test for the presence of for example, Gram-Positive bacteria, Gram-Negative bacteria, yeast, and/or any other organism and subsequently tested using, for example, a polymerase chain reaction (PCR)-based system to identify a specific organism. In some instances, the culture bottle can receive a bodily-fluid sample and the culture medium (disposed therein) can be tested for the presence of any suitable organism. If such a test of the culture medium yields a positive result, the culture medium can be subsequently tested using a PCR-based system to identify a specific organism.

The needle 120 of the transfer device 100 has a proximal end portion 121 and a distal end portion 122 and defines the lumen 123 therebetween. The proximal end portion 121 can physically and fluidically couple the needle 120 to the housing 101 (e.g., it can be the lock mechanism as described above). In some embodiments, a portion of the housing 101 can be formed about the proximal end portion 121 of the needle 120, thereby coupling the needle 120 to the housing 101. For example, in some embodiments, the needle 120 can be formed from a metal (e.g., stainless steel or the like) or engineered plastics (e.g. polymers, thermoplastics, glass-filled polymers, carbon-filled polymers, ceramic-based polymers, etc.) and the housing 101 can be formed from thermoplastics (e.g., polyethylene, polypropylene, polyamide, polycarbonate, silicone, urethane and silicon/urethane copolymer (hybrid) materials or the like). In such embodiments, the housing 101 can be, for example, over-molded about the proximal end portion 121 of the needle 120 to fixedly couple the needle 120 to the housing 101.

The distal end portion 122 of the needle 120 can be inserted into a portion of a patient to deliver a fluid to or receive a fluid from the patient. For example, in some embodiments, the distal end portion can include a tip with a sharp point (e.g., a beveled tip) configured to pierce a portion of the patient to dispose the distal end portion 122 within, for example, a vein. In other embodiments, a piercing member (e.g., a lumen defining needle) can be movably disposed within the needle 120 to facilitate the insertion of the distal end portion 120 into the portion of the patient (e.g., a trocar). In some embodiments, at least a portion (e.g., the distal end portion) of the needle 120 can include an antibiotic formulated to kill bacteria dislodged during venipuncture and prevent contamination of the fluid sample and/or the patient. For example, an exterior surface of the needle 120 and/or a portion of the lumen 123 can include a coating that included that antibiotic. In some embodiments, the piercing member (e.g., a trocar) can include a coating that included that antibiotic. The distal end portion 122 of the needle 120 can define one or more openings that place the lumen 123 of the needle 120 in fluid communication with a volume outside of the needle 120. For example, in some embodiments, the distal end (e.g., the tip) is substantially open. In other embodiments, the distal end can be closed and the needle 120 can define one or more openings along the circumference of the needle 120 (i.e., along the sidewalls of the needle 120). In such embodiments, the openings can be arranged in any suitable manner. For example, in some embodiments, the openings can be linearly arranged along a length of the needle 120. In other embodiments, the openings can be arranged in a linear manner along the circumference of the needle 120 (e.g., perpendicular to the length of the needle 120). In still other embodiments, the openings can be disposed in a non-linear arrangement.

The occlusion mechanism 140 of the transfer device 100 can be included in or coupled to the housing 101. In some embodiments, the occlusion mechanism 140 can be at least partially disposed within the housing 101. The occlusion mechanism 140 can be any suitable mechanism configured to direct, obstruct, or otherwise control a flow of a fluid. More specifically, the occlusion mechanism 140 includes an occlusion member 141 that can be moved (e.g., pushed, pulled, rotated, slid, bent, or otherwise reconfigured) between a first configuration (FIG. 1) and a second configuration (FIG. 2). In some embodiments, the occlusion member 141 is manually moved. In other embodiments, the occlusion member 141 is urged to move by an actuation of a portion of the occlusion mechanism 140. In still other embodiments, the occlusion member 140 can automatically transform (e.g., reconfigure) from the first configuration to the second configuration, as described in further detail herein.

While in the first configuration, the occlusion member 141 can fluidically isolate at least a portion of the lumen 123 defined by the needle 120 from the fluid flow path 108 defined by the housing 101 and, once moved to the second configuration (FIG. 2), the occlusion member 141 can allow the lumen 123 of the needle 120 to be in fluid communication with the fluid flow path 108 of the housing 101. For example, in some embodiments, when in the first configuration, the occlusion member 141 can be at least partially disposed within the lumen 123 of the needle 120 such that a portion of the lumen 123 that is distal to the occlusion member 141 is fluidically isolated from the fluid flow path 108 defined by the housing 101. In such embodiments, when in the second configuration, the occlusion member 141 can be removed from the lumen 123 such that substantially the entire lumen 123 of the needle 120 is in fluid communication with the fluid flow path 108 defined by the housing 101 (see e.g., FIG. 2).

While the occlusion member 141 is shown in FIGS. 1 and 2 as being disposed within the needle 120, in other embodiments, the occlusion member 141 can be disposed about at least a portion of the needle 120. For example, in some embodiments, the occlusion member 141 can form a sheath or the like that substantially surrounds at least a portion of the needle 120. In such embodiments, when in the first configuration, the occlusion member 141 can block or surround the one or more openings (described above) defined by the needle 120 and can moved relative to the needle 120 (i.e., to the second configuration) to substantially expose the one or more openings. In this manner, the lumen 123 of the needle 120 can be maintained in fluid communication with the fluid flow path 108 of the housing 101 and the occlusion member 141 can fluidically isolate the lumen 123 of the needle 120 from a volume substantially outside of the needle 120. In some embodiments, a portion of the needle 120 can form the occlusion mechanism 140. For example, at least a portion of the needle 120 can be formed from a memory shape alloy that reconfigures when exposed to given conditions (e.g., can move to form an opening when exposed to a temperature within the body). In other embodiments, at least a portion of the needle 120 can be configured to dissolve when exposed to a bodily fluid (e.g., a coating disposed about a portion of the needle 120 such that when the distal end portion 122 is inserted into the patient, the coating is placed in contact with a bodily fluid and thereby is dissolved).

In use, the occlusion member 141 can be in the first configuration to fluidically isolate at least a portion of the lumen 123 of the needle 120 from the fluid flow path 108 defined by the housing 101. The distal end portion 122 of the needle 120 can be inserted into a portion of the patient to be disposed within, for example, a vein. In this manner, dermally residing microbes dislodged during a venipuncture event (e.g., when the needle 120 and/or the occlusion member 141 pierces the skin of the patient) are isolated from the fluid flow path 108 of the housing 101. Once the distal end portion 122 of the needle 120 is disposed within the vein, the occlusion member 141 can be moved to the second configuration, as indicated by the arrow AA in FIG. 2. For example, the occlusion member 141 can be in the first configuration within a portion of the lumen 123 of the needle 120 when the needle 120 is inserted into the vein and the occlusion member 141 can be substantially removed from the lumen 123 of the needle 120 to place the transfer device 100 in the second configuration. In this manner, the lumen 123 of the needle 120 is placed in fluid communication with a bodily fluid and also placed in fluid communication with the fluid flow path 108 of the housing 101.

While not shown in FIGS. 1 and 2, in some embodiments, the occlusion mechanism 140 can include an actuator configured to move the occlusion member 141 between the first and second configuration. For example, in some embodiments, an actuator can be a push button, a slider, a toggle, a pull-tab, a handle, a dial, a lever, an electronic switch, or any other suitable actuator. In this manner, the actuator can be movable between a first position corresponding to the first configuration of the occlusion member 141, and a second position, different from the first position, corresponding to the second configuration of the occlusion member 141. In some embodiments, the actuator can be configured for uni-directional movement. For example, the actuator can be moved from its first position to its second position, but cannot be moved from its second position back to its first position. In this manner, the occlusion member 140 is prevented from being moved to its second configuration before its first configuration.

While shown in FIGS. 1 and 2 as being moved in a transverse direction perpendicular to a length of the needle 120 (e.g., in the direction of the arrow AA), in other embodiments, the occlusion member 141 can be moved between the first configuration and the second configuration in any suitable manner or direction. For example, in some embodiments, the occlusion member 141 can be moved in a rotational motion between the first configuration and the second configuration. In other embodiments, the occlusion member 141 can be moved in a proximal or distal direction (e.g., substantially perpendicular to the direction of the arrow AA).

Although not shown in FIGS. 1 and 2, in some embodiments, the transfer device 100 and/or a portion thereof can be included in any suitable transfer device or system that is configured to withdraw a sample of bodily fluid from a patient and/or configured to parenterally deliver a fluid to the patient. For example, in some embodiments, the transfer device 100 and/or portion thereof can be included in any of the transfer devices described in U.S. Provisional Patent Application 61/947,076, entitled, "Apparatus and Methods for Disinfection of a Specimen Container," filed Mar. 3, 2014, U.S. patent application Ser. No. 14/096,826 entitled, "Sterile Bodily-Fluid Collection Device and Methods," filed Dec. 4, 2013, or U.S. Pat. No. 8,535,241, entitled "Fluid Diversion Mechanism for Bodily-Fluid Sampling," filed Oct. 12, 2012 the disclosures of which are incorporated herein by reference in their entireties. Thus, the transfer device 100 can be used in conjunction with any suitable transfer device to withdraw a sample of bodily fluid from a patient and/or parenterally deliver a fluid to the patient with reduced contamination from, for example, dermally residing microbes, undesirable bodily tissue, and/or the like.

Figure 3:
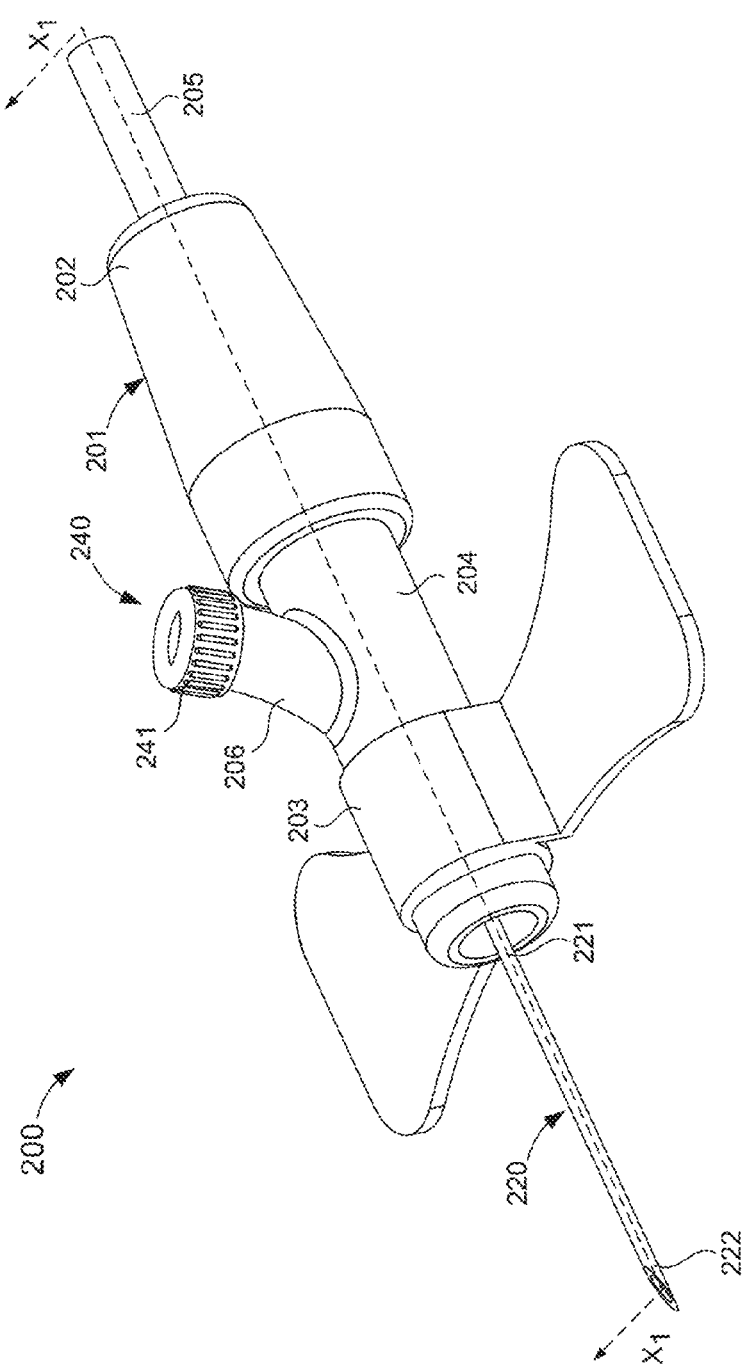
FIG. 3 is a perspective view of a fluid transfer device in according to an embodiment.
Figure 4:
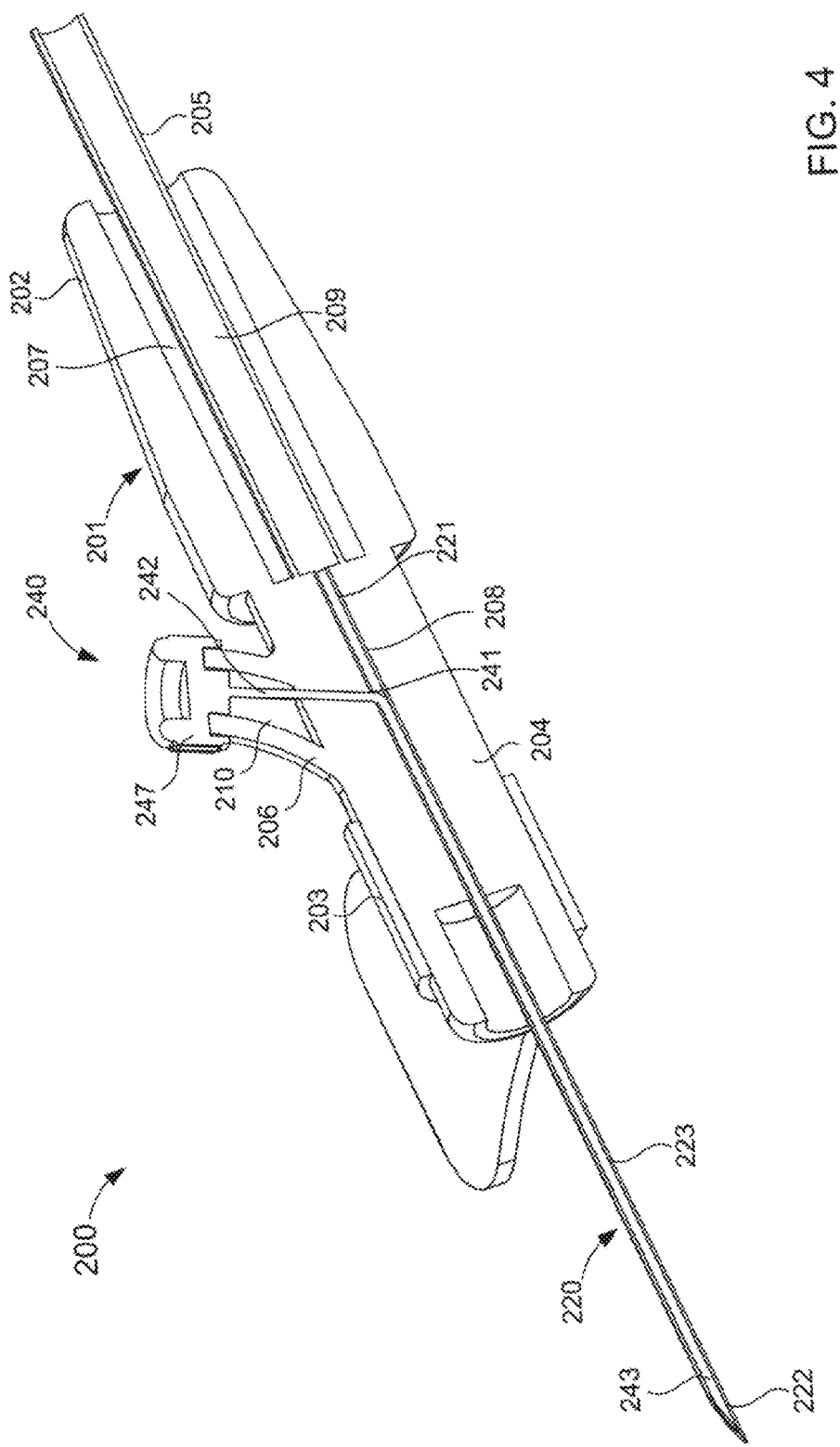
FIG. 4 is a cross-sectional view of the fluid transfer device of FIG. 3 taken along the like $X_1$-$X_1$, while in a first configuration.
Figure 5:
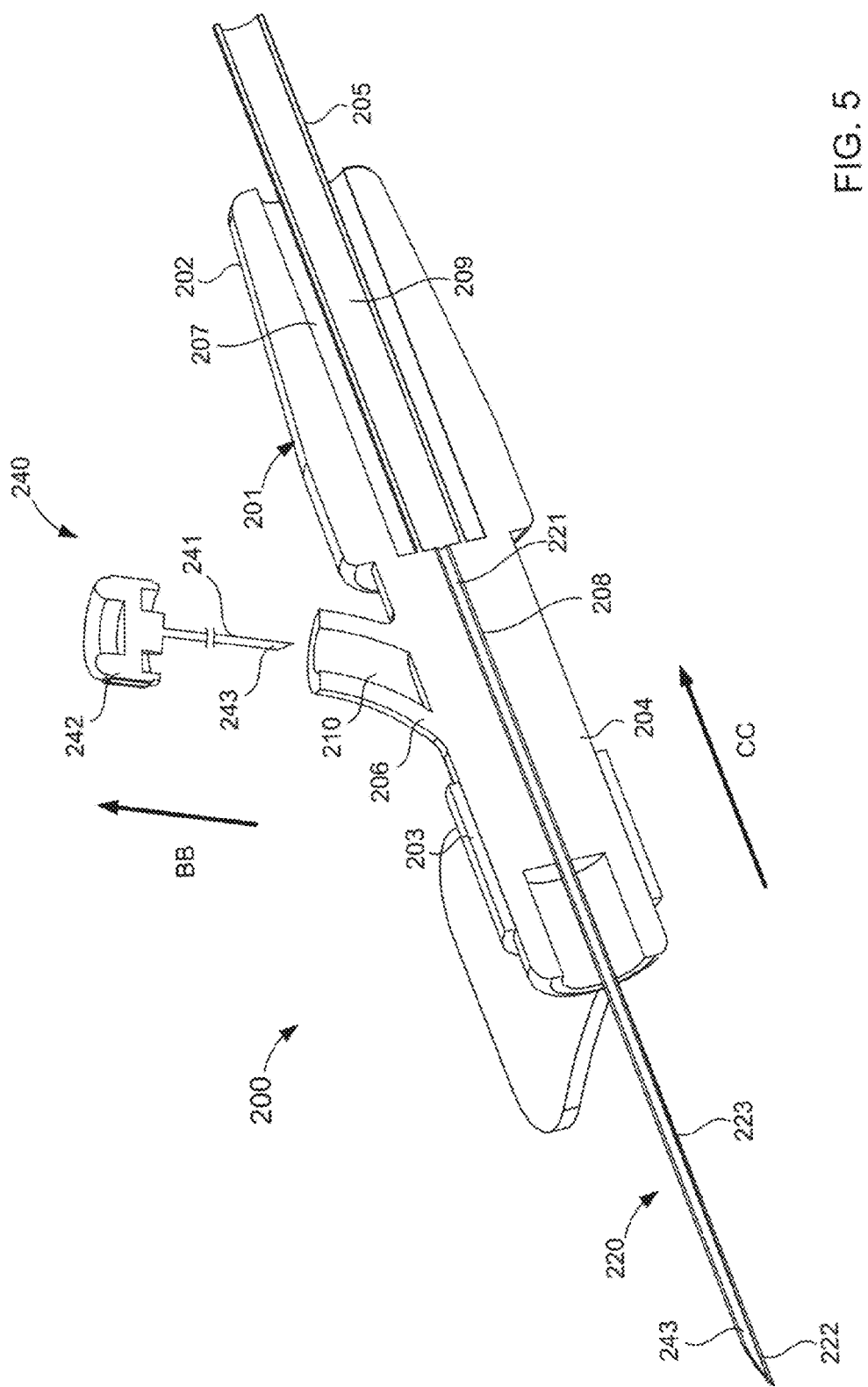
FIG. 5 is a cross-sectional view of the fluid transfer device of FIG. 3 taken along the line $X_1$-$X_1$, while in a second configuration.

FIGS. 3-5 illustrate a fluid transfer device 200 (also referred to herein as "transfer device") according to an embodiment. The transfer device 200 includes a housing 201, a needle 220, and an occlusion mechanism 240. The needle 220 has a proximal end portion 221 and a distal end portion 222 and defines a lumen 223 therebetween. The proximal end portion 221 of the needle 220 is physically and fluidically coupled to a distal end portion 203 of the housing 201, as described above with reference to FIGS. 1 and 2. The distal end portion 222 is configured to be inserted into a patient such that a fluid can be transferred to or from the patient via the lumen 223 of the needle 220, as described in further detail herein.

The housing 201 includes a proximal end portion 202, the distal end portion 203, and a medial portion 204. As shown in FIG. 3, the housing 201 can have an overall shape substantially similar to known butterfly needles. The housing 201 can be any suitable shape, size, or configuration. For example, while shown in FIG. 3 as being substantially cylindrical, the housing 201 can be square, rectangular, polygonal, and/or any other non-cylindrical shape. In this manner, the overall shape of the housing 201 can facilitate the handling of the transfer device 201 by including similar geometric features as known butterfly needles. The distal end portion 203 of the housing 201 can be physically and fluidically coupled to a proximal end portion 221 of the needle 220, as described above. The proximal end portion 202 can be coupled to a cannula 205. For example, as shown in FIGS. 4 and 5, a portion of the cannula 205 can be disposed within an opening 207 defined by the proximal end portion 202 of the housing 201. When disposed within the opening 207, the cannula 205 can be physically and fluidically coupled to the medial portion 204 of the housing 201. More specifically, the cannula 205 defines a lumen 209 that is placed in fluid communication with a fluid flow path 208 defined by the medial portion 204 of the housing 201 when the cannula 205 is physically and fluidically coupled thereto.

The medial portion 204 of the housing 201 includes a port 206 that can be coupled to and/or that can receive a portion of the occlusion mechanism 240. Expanding further, the occlusion mechanism 240 can be, for example, a sty let that includes an engagement member 247 that is coupled to an occlusion member 241. As shown in FIG. 4, a portion of the occlusion member 241 is disposed within an opening 210 defined by the port 206 to place the engagement member 247 in contact with the port 206. The engagement member 247 can be coupled to the port 206 in any suitable manner. For example, in some embodiments, a surface of the engagement member 247 and a surface of the port can form a threaded coupling, a press fit (i.e., a friction fit), a snap fit, any number of mating recesses, and/or the like. As described in further detail herein, the occlusion mechanism 240 can be moved between a first configuration associated with a first configuration of the transfer device 200 (see e.g., FIG. 4) and a second configuration associated with a second configuration of the transfer device 200 (see e.g., FIG. 5).

As shown in FIG. 4, when the engagement member 247 of the occlusion mechanism 240 is coupled to the port 206 (e.g., the first configuration), a proximal end portion 242 of the occlusion member 241 is disposed within the opening 210 and the occlusion member 241 can extend within the fluid flow path 208 of the housing 201 and the lumen 223 defined by the needle 220. More specifically, the occlusion member 241 can extend within the lumen 223 of the needle 220 such that a distal end portion 243 of the occlusion member 241 is substantially aligned with the distal end portion 222 of the needle 220. Said another way, a distal end surface of the occlusion member 241 can be substantially parallel and aligned (e.g., coplanar) with a distal end surface of the needle 220.

The arrangement of the occlusion member 241 can be such that an outer surface of the occlusion member 241 is in contact with an inner surface of the needle 220 that defines the lumen 223. In this manner, the outer surface of the occlusion member 241 and the inner surface of the needle 220 can form a friction fit. Said another way, the outer diameter of at least the distal end portion 243 of the occlusion member 240 can be slightly larger than the inner diameter of at least the distal end portion 222 of the needle 220, thus, the occlusion member 241 and the needle 220 can form a friction fit (at least at the distal end portion 222 of the needle 220). Therefore, when the distal end portion 243 of the occlusion member 241 is aligned with the distal end portion 222 of the needle 220 the lumen 223 is substantially fluidically isolated from a volume outside of the needle 220 (e.g., a volume disposed proximally relative to the needle 220). In other words, the lumen 223 of the needle 220 is Obstructed by the occlusion member 241.

In use, the transfer device 200 can be in the first configuration (FIG. 4) and a proximal end portion of the cannula 205 can be physically and fluidically coupled to a fluid reservoir (not shown). The fluid reservoir can be any suitable fluid reservoir such as, for example, known fluid reservoirs configured to receive a bodily fluid from a patient and/or configured to deliver a parenteral fluid to the patient. In some embodiments, the fluid reservoir can be, for example, a Vacutainer®, a BacT/ALERT® SN, a BacT/ALERT® FA, and/or any of the containers, vials, bottles, reservoirs, etc. described above with reference to fluid reservoir 130 of FIGS. 1 and 2. In some embodiments, the external fluid reservoir can be configured such that a negative pressure exists within an inner volume of the reservoir. In other embodiments, the fluid reservoir can contain a liquid that is intended to be delivered to the patient. The fluid reservoir can be coupled to the cannula 205 in any suitable manner. For example, in some embodiments, the cannula 205 can be disposed about a port of the fluid reservoir. In other embodiments, the proximal end portion cannula 205 can include a Luer Lok® (not shown) that is configured to matingly couple to the fluid reservoir. In still other embodiments, the proximal end portion of the cannula 205 can include a piercing member (not shown) that is configured to pierce a piercable septum (e.g., such as those included in a Vacutainer®).

With the cannula 205 coupled to the fluid reservoir and with the transfer device 200 and the occlusion mechanism 240 in the first configuration, a user (e.g., a physician, a nurse, a technician, a phlebotomist, or the like) can manipulate the transfer device 200 to insert the needle 220 into a patient. In this manner, the distal end portion 222 of the needle 220 can pierce the skin of the patient to dispose the distal end portion 222 of the needle 220 within, for example, a vein. In some instances, the venipuncture event (e.g., the insertion of the distal end portion 222 of the needle 220 into the vein) can dislodge, for example, dermally residing microbes from the insertion point. Thus, with the occlusion mechanism 240 in the first configuration where the occlusion member 241 obstructs the lumen 223 of the needle 220, the lumen 223 is isolated from the dislodged dermally residing microbes and/or other undesirable external contaminants that may be present on a patient's skin surface (e.g. contaminants, bacteria, fungus, yeast, etc. from: ambient air, healthcare practitioner's finger transferred when palpating or re-palpating the patient's vein, transferred onto collection supplies during assembly and/or when opening packaging, etc.).

With the distal end portion 222 of the needle 220 disposed within the vein, the occlusion mechanism 240 can be moved to the second configuration to place the transfer device in the second configuration, as indicated by the arrow BB in FIG. 5. For example, the engagement member 247 of the occlusion mechanism 240 can be decoupled from the port 206 (e.g., unthreaded or pulled) and moved in the direction of the arrow BB such that the occlusion member 241 is removed from the lumen 223 of the needle 220 and the fluid flow path 208 of the housing 201. While not shown in FIGS. 3-5, the medial portion 204 can include, for example, a self-sealing septum that is configured to seal an opening that remains from the removal of the occlusion member 241. Therefore, with the cannula 205 fluidically coupled to the fluid reservoir (not shown), the movement of the occlusion mechanism 240 to the second configuration places the lumen 223 of the needle 220 in fluid communication with the vein of the patient as well as in fluid communication with the fluid reservoir e.g., via the fluid flow path 208 of the housing 201 and the lumen 209 of the cannula 205), as indicated by the arrow CC in FIG. 5. Said another way, the lumen 223 of the needle 220 is substantially unobstructed such that a flow of fluid substantially free from contaminants (e.g., dermally residing microbes and/or other undesirable external contaminants) can be transferred to or from the patient via the lumen 223 of the needle 220, the fluid flow path 208 of the housing 201, and the lumen 209 of the cannula 205.

Although not shown in FIGS. 3-5, in some embodiments, the transfer device 200 and/or a portion thereof can be included in any suitable transfer device or system that is configured to withdraw a sample of bodily fluid from and/or parenterally deliver a fluid to a patient, which is substantially free of contamination from, for example, dermally residing microbes, undesirable bodily tissue, and/or the like. For example, in some embodiments, the transfer device 200 and/or portion thereof can be included in any of the transfer devices described above with reference to the transfer device 100 in FIGS. 1 and 2.

While the occlusion member 240 is shown in FIG. 5 as being manually moved from the first configuration to the second configuration, in other embodiments, a transfer device can include an occlusion mechanism that has an actuator operable in moving the occlusion mechanism from a first configuration to a second configuration. For example, FIGS. 6-12 illustrate a fluid transfer device 300 (also referred to herein as "transfer device") according to an embodiment. The transfer device 300 includes a housing 301, a needle 320, and an occlusion mechanism 340. The needle 320 has a proximal end portion 321 and a distal end portion 322 and defines a lumen 323 therebetween. The proximal end portion 321 of the needle 320 is physically and fluidically coupled to a shuttle member 360 of the occlusion member 340, as described in further detail herein. The distal end portion 322 is configured to be inserted into a patient such that a fluid can be transferred to or from the patient via the lumen 323 of the needle 320, as described in further detail herein.

Figure 6:
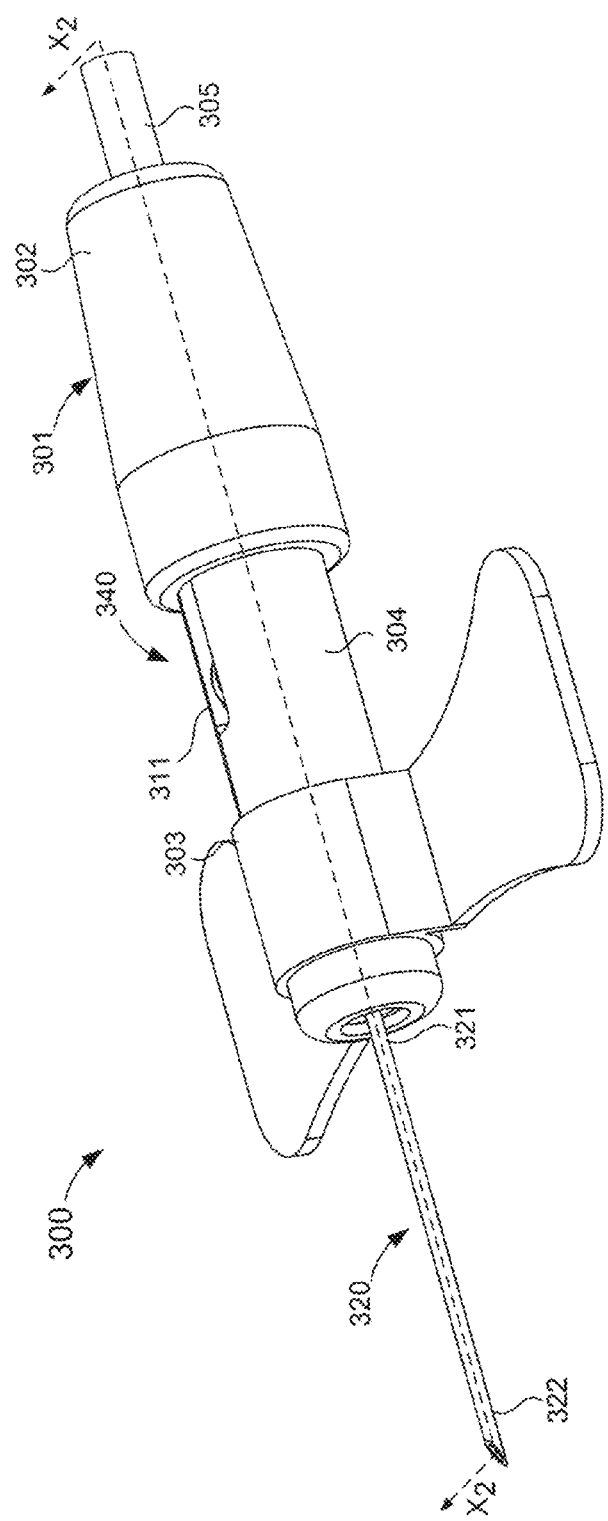
FIG. 6 is a perspective view of a fluid transfer device in according to an embodiment.
Figure 7:
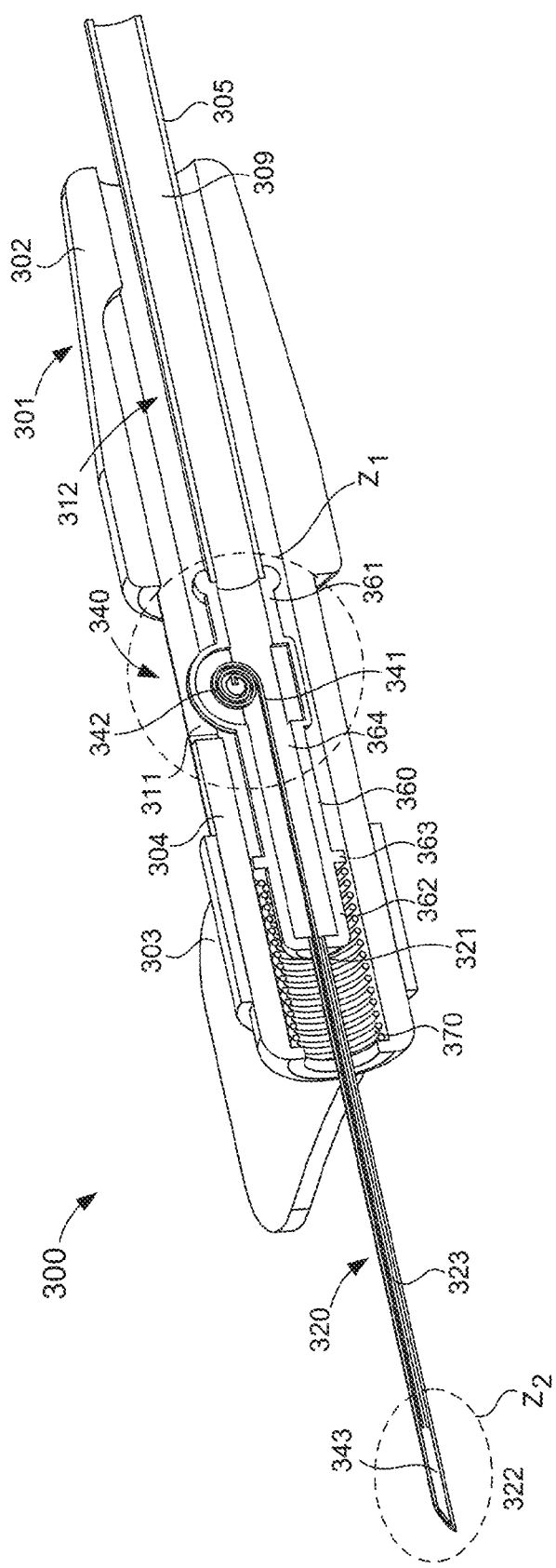
FIG. 7 is a cross-sectional view of the fluid transfer device of FIG. 6 taken along the like $X_2$-$X_2$, while in a first configuration.

The housing 301 has a proximal end portion 302, a distal end portion 303, and a medial portion 304. As shown in FIG. 6, the housing 301 can have an overall shape that is substantially similar to the housing 201 shown and described with reference to FIG. 3. As shown in FIG. 7, the housing 301 defines an inner volume 312 between the proximal end portion 302 and the distal end portion 303 that substantially encloses and/or houses the occlusion mechanism 340 and a bias member 370. The proximal end portion 302 and the distal end portion 303 of the housing 301 are substantially open. In this manner, the distal end portion 303 can receive the proximal end portion 321 of the needle 320 that can then be physically and fluidically coupled to a distal end portion 362 of the shuttle member 360. The proximal end portion 302 can receive a portion of a cannula 305 that can then be physically and fluidically coupled to a proximal end portion 361 of the shuttle member 360. As shown in FIGS. 6 and 7, the housing 301 also defines a slot 311 that can movably receive a retraction portion 365 of the shuttle member 360 when the occlusion mechanism 340 is moved between a first configuration and a second configuration, as described in further detail herein. Thus, the overall size of the housing 301 can remain substantially similar to, for example, known butterfly needles while disposing the occlusion mechanism 340 within the inner volume 312 of the housing 301.

The occlusion mechanism 340 includes an occlusion member 341 and the shuttle member 360. As described above, the distal end portion 362 of the shuttle member 360 is physically and fluidically coupled to the proximal end portion 321 of the needle 320. The needle 320 can be coupled to the shuttle member 360 in any suitable manner, such as, for example, those described above with reference to FIGS. 1 and 2. In other embodiments, at least a portion of the shuttle member 360 can be monolithically formed with the needle 320. For example, in some embodiments, at least the portion of the shuttle 360 and the needle 320 can be formed from a thermoplastic such as those described above with reference to FIGS. 1 and 2. In such embodiments, the needle 320 can be, for example, a cannula having a sharpened distal end.

As shown in FIG. 7, the shuttle member 360 includes a flange 363 that can be in contact with the bias member 370 (e.g., a spring or the like) disposed within the inner volume 312 of the housing 301. More specifically, the bias member 370 can be disposed between an inner distal surface of the housing 301 and a surface of the flange 363. In some instances, the bias member 370 can be actuated, either directly or indirectly, to move from a first configuration. (e.g., a compressed configuration) to a second configuration (e.g., an expanded configuration). In such instances, the movement of the bias member 370 urges the shuttle member 360 to move from a first position relative to the housing 301 to a second position relative to the housing 301. For example, in some embodiments, the shuttle member 360 can be moved relative to the housing 301 to withdraw the needle 320 and/or the occlusion member 341 after being inserted into the body of a patient. Expanding further, in some embodiments, the housing 301 can include or be coupled to a cannula (not shown in FIGS. 6-12) that can be adjacent to the needle 320. In such embodiments, the needle 320 can be operable in a venipuncture event and then can be withdrawn (with or without the occlusion member 341) when the shuttle member 360 is moved to the second position relative to the housing 301, thereby leaving the cannula disposed within the patient.

Figure 8:
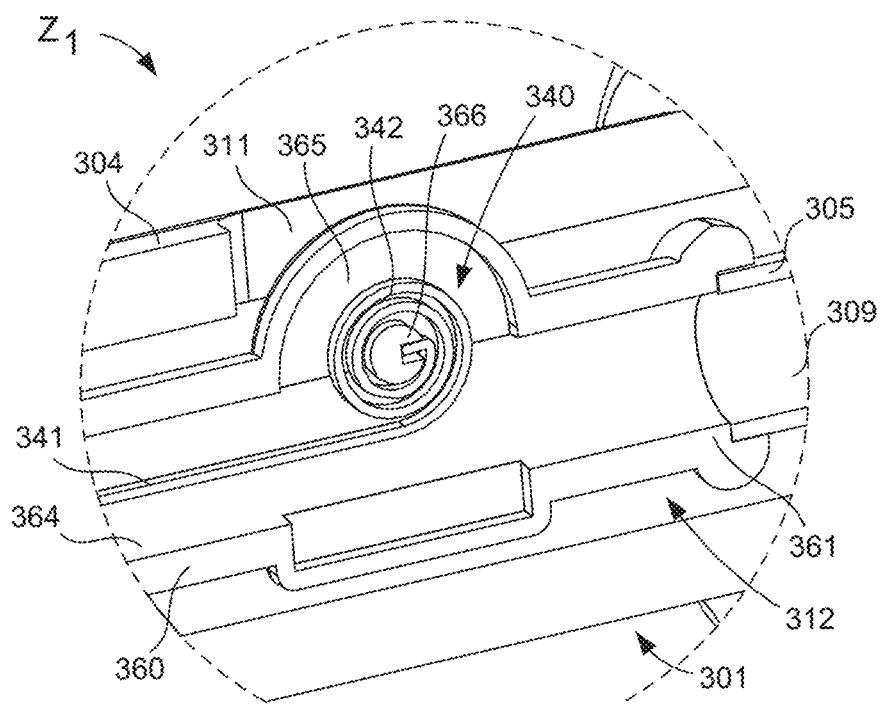
FIG. 8 is an enlarged view of a portion of the fluid transfer device of FIG. 6 in the first configuration and identified in FIG. 7 as region $Z_1$.

As shown in FIGS. 7-11, the occlusion member 341 has a proximal end portion 342 and a distal end portion 343 and can move between a first configuration and a second configuration. The proximal end portion 342 of the occlusion member 341 is coupled to a coupling protrusion 366 that extends from a surface of the retraction portion 365 of the shuttle member 360. As shown in FIG. 8, the proximal end portion 342 of the occlusion member 341 can be disposed within a channel defined by the coupling protrusion 366 to couple the occlusion member 341 thereto. For example, the proximal end portion 342 of the occlusion member 341 can form a press fit with a surface of the coupling protrusion 366 that defines the channel. In some embodiments, a preloaded stress within the proximal end portion 342 of the occlusion member 341 can maintain the proximal end portion 342 in contact with the surface of the coupling protrusion 366 defining the channel. Thus, at least a portion of the occlusion member 341 can be coiled about the coupling protrusion 366, as shown in FIG. 8. As described in further detail herein, the occlusion member 341 can be actuated to move from the first configuration to the second configuration such that a larger portion of the occlusion member 341 is coiled (i.e., wrapped) about the coupling protrusion 366 of the shuttle member 360.

Figure 9:
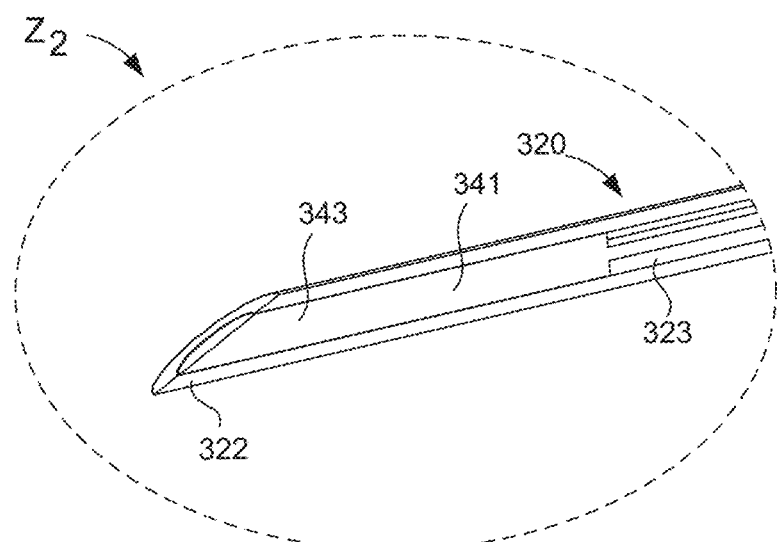
FIG. 9 is an enlarged view of a portion of the fluid transfer device of FIG. 6 in the first configuration and identified in FIG. 7 as region $Z_2$.

While in the first configuration, the distal end portion 343 of the occlusion member 341 is disposed within the lumen 323 of the needle 320. As shown in FIG. 9, the occlusion member 341 can extend within the lumen 323 of the needle 320 such that a distal end portion 343 of the occlusion member 341 is substantially aligned with the distal end portion 322 of the needle 320. The arrangement of the occlusion member 341 and the needle 320 can be substantially similar to or the same as the arrangement of the occlusion member 241 and the needle 220 described above with reference to FIGS. 4 and 5. Thus, when the distal end portion 343 of the occlusion member 341 is aligned with the distal end portion 322 of the needle 320 the lumen 323 is substantially fluidically isolated from a volume outside of the needle 320 (e.g., a volume disposed proximally relative to the needle 320). In other words, the lumen 323 of the needle 320 is obstructed by the occlusion member 341.

In use, the transfer device 300 can be in the first configuration (FIG. 7) and a proximal end portion of the cannula 305 can be physically and fluidically coupled to a fluid reservoir (not shown). The fluid reservoir can be any suitable fluid reservoir such as, for example, those described above with reference to the fluid reservoir 130 of FIGS. 1 and 2.

With the cannula 305 coupled to the fluid reservoir and with the transfer device 300 and the occlusion member 341 in the first configuration, a user (e.g., a physician, a nurse, a technician, a phlebotomist, or the like) can manipulate the transfer device 300 to insert the needle 320 into a patient. In this manner, the distal end portion 322 of the needle 320 can pierce the skin of the patient to dispose the distal end portion 322 of the needle 320 within, for example, a vein. In some instances, the venipuncture event (e.g., the insertion of the distal end portion 322 of the needle 320 into the vein) can dislodge, for example, dermally residing microbes from the insertion point. Thus, with the occlusion member 341 in the first configuration where the occlusion member 341 obstructs the lumen 323 of the needle 320, the lumen 323 is isolated from the dislodged dermally residing microbes and/or other undesirable external contaminants.

Figure 10:
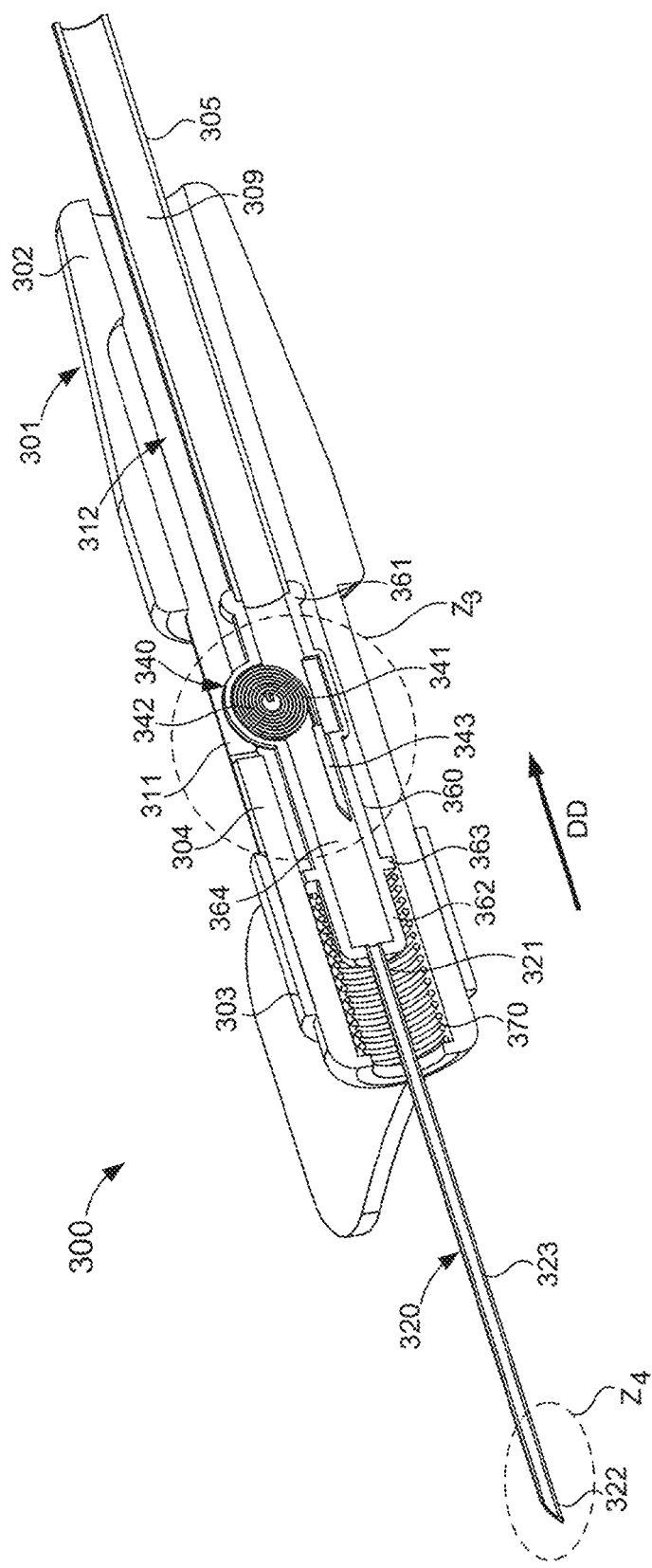
FIG. 10 is a cross-sectional view of the fluid transfer device of FIG. 6 taken along the line $X_2$-$X_2$, while in a second configuration.
Figure 11:
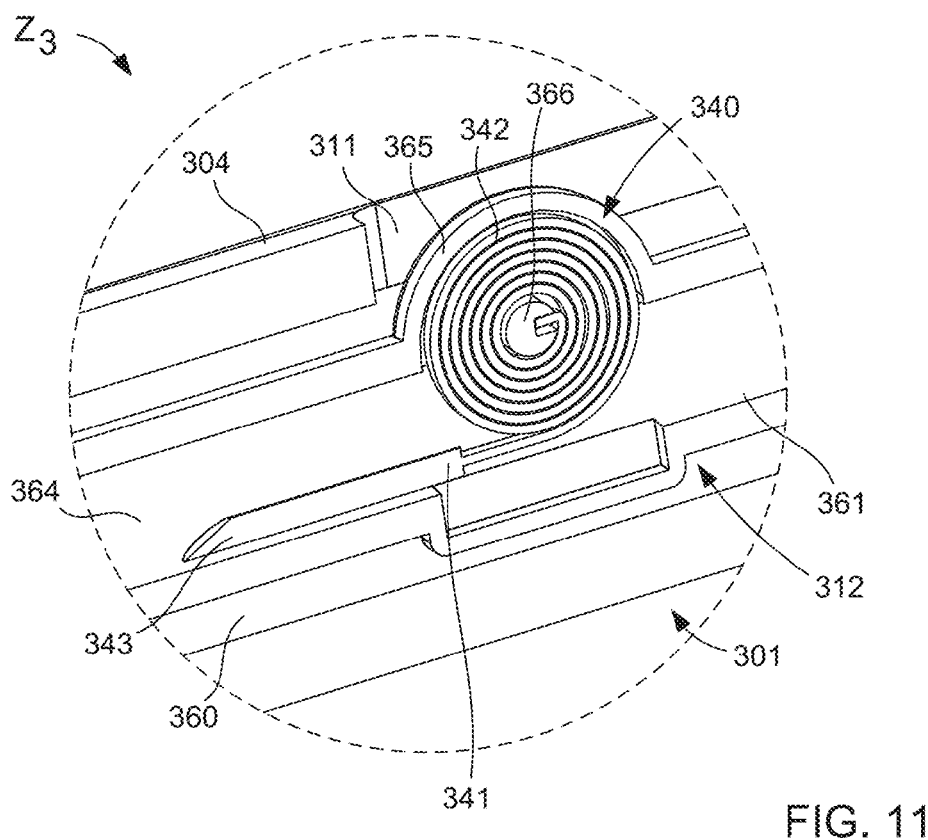
FIG. 11 is an enlarged view of a portion of the fluid transfer device of FIG. 6 in the second configuration and identified in FIG. 10 as region $Z_3$.
Figure 12:
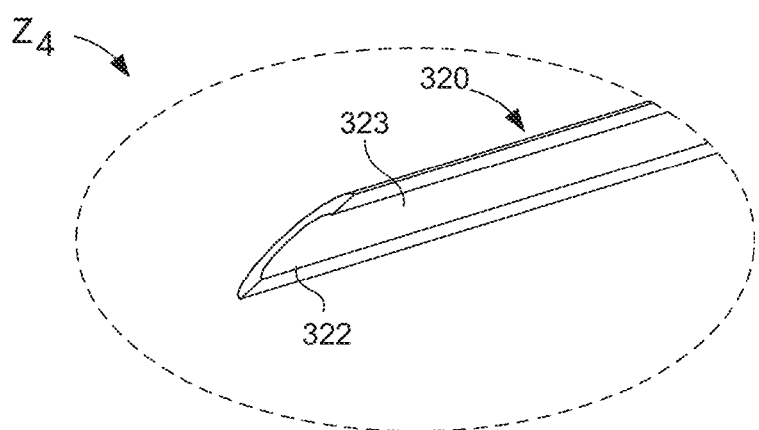
FIG. 12 is an enlarged view of a portion of the fluid transfer device of FIG. 6 in the first configuration and identified in FIG. 10 as region $Z_4$.

With the distal end portion 322 of the needle 320 disposed within the vein, the occlusion member 341 can be moved to the second configuration to place the transfer device 300 in the second configuration, as indicated by the arrow DD in FIG. 10. For example, the user can manipulate an actuator (not shown in FIGS. 6-12) that is operable in moving the occlusion member 341 from the first configuration to the second configuration. In some embodiments, the actuator can be a push button, a toggle, a slide, an electric circuit, or any other suitable actuator. In some embodiments, the user can, for example, squeeze a region of the medial portion 304 of the housing 301 to actuate the occlusion member 341. In this manner, the occlusion member 341 can coil about the coupling protrusion 366 of the retraction portion 365 of the shuttle member 360, as shown in FIG. 11. The coiling motion of the occlusion member 341 moves the distal end portion 343 of the occlusion member 341 in the proximal direction (e.g., the direction of the arrow DD in FIG. 10), thereby removing the distal end portion 343 of the occlusion member 341 from the lumen 323 of the needle 320 (see e.g., FIGS. 11 and 12).

Therefore, with the cannula 305 fluidically coupled to the fluid reservoir (not shown), the movement of the occlusion member 341 to the second configuration places the lumen 323 of the needle 320 in fluid communication with the vein of the patient as well as in fluid communication with the fluid reservoir. Expanding further, the proximal end portion 322 of the needle 320 is physically and fluidically coupled to the shuttle member 360 (as described above) such that when the occlusion member 341 is in the second configuration (e.g., the distal end portion 322 is disposed within the lumen 364 of the shuttle member 360 (FIG. 11)), the lumen 323 of the needle 320 is placed in fluid communication with the fluid reservoir. In this manner, the lumen 323 of the needle 320 is substantially unobstructed such that a flow of fluid substantially free from contaminates (e.g., dermally residing microbes) can be transferred to or from the patient via the lumen 323 of the needle 320, the lumen 364 of the shuttle member 360, and the lumen 309 of the cannula 305.

As described above, in some instances, once the needle 320 is disposed within the vein of the patient, the user can manipulate the transfer device 300 to move the shuttle member 360 from the first position to the second position relative to the housing 301. Thus, the needle 320 and the occlusion mechanism 340 can be retracted (i.e., moved in the proximal direction) relative to the housing 301. In some embodiments, the arrangement of the transfer device 300 can be such that a cannula coupled to the distal end portion 303 of the housing 301 is maintained within the vein while the needle 320 and the occlusion mechanism 340 are retracted.

Although not shown in FIGS. 6-12, in some embodiments, the transfer device 300 and/or a portion thereof can be included in any suitable transfer device or system that is configured to withdraw a sample of bodily fluid from and/or parenterally deliver a fluid to a patient, which is substantially free of contamination from, for example, dermally residing microbes, undesirable bodily tissue, and/or the like. For example, in some embodiments, the transfer device 300 and/or portion thereof can be included in any of the transfer devices described above with reference to the transfer device 100 in FIGS. 1 and 2.

While the occlusion member 341 is shown and described above with reference to FIGS. 6-12 as being disposed within the lumen 323 of the needle 320, in other embodiments, a transfer device can include an occlusion member that is disposed about a needle. In other words, the needle of the transfer device can be disposed within a lumen of the occlusion member. For example, FIGS. 13-17 illustrate a fluid transfer device 400 (also referred to herein as "transfer device" according to an embodiment). The transfer device 400 includes a housing 401, a needle 420, and an occlusion mechanism 440 (also referred to herein as "occlusion member"). The needle 420 has a proximal end portion 421 and a distal end portion 422 and defines a lumen 423 therebetween. The proximal end portion 421 of the needle 420 is physically and fluidically coupled to a distal end portion 403 of the housing 401, as described above with reference to FIGS. 1 and 2. The distal end portion 422 of the needle 420 defines a set of openings or apertures 425 disposed along a circumference of the needle 420 that place the lumen 423 of the needle 420 in fluid communication with a volume outside of the needle 420. More specifically, the distal end portion 422 of the needle 420 has a solid (i.e., closed) tip 424 (see e.g., FIG. 15) that obstructs the distal end of the needle 420. Thus, the openings 425 disposed about the circumference of the needle 420 place the lumen 423 in fluid communication with a volume outside of the needle 420 rather than needles 220 and 320 shown above that have a distal end surface that is open. In this manner, the needle 420 can be inserted into a patient such that a fluid can be transferred to or from the patient via the openings 425 and the lumen 423 of the needle 420, as described in further detail herein.

Figure 13:
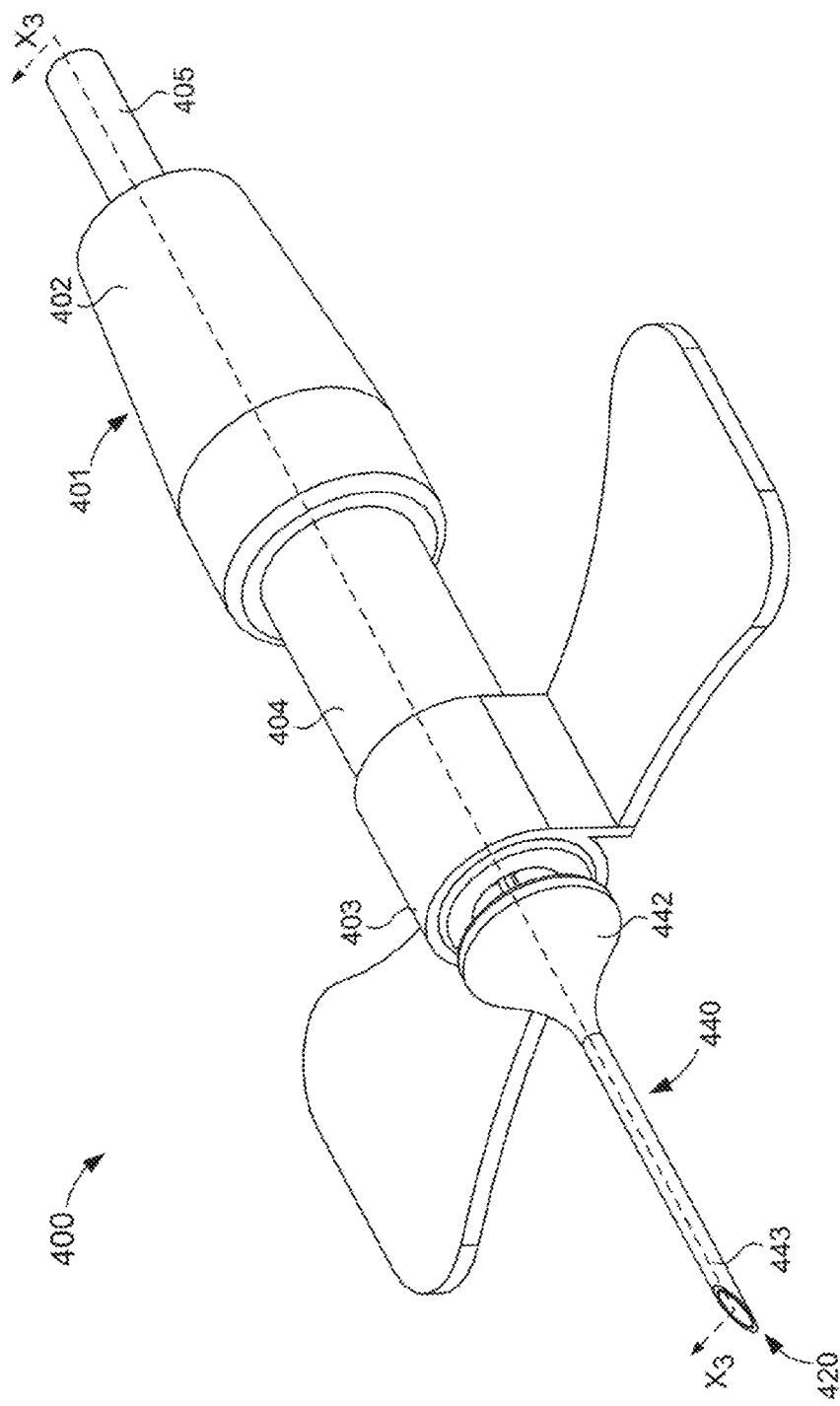
FIG. 13 is a perspective view of a fluid transfer device in according to an embodiment.
Figure 14:
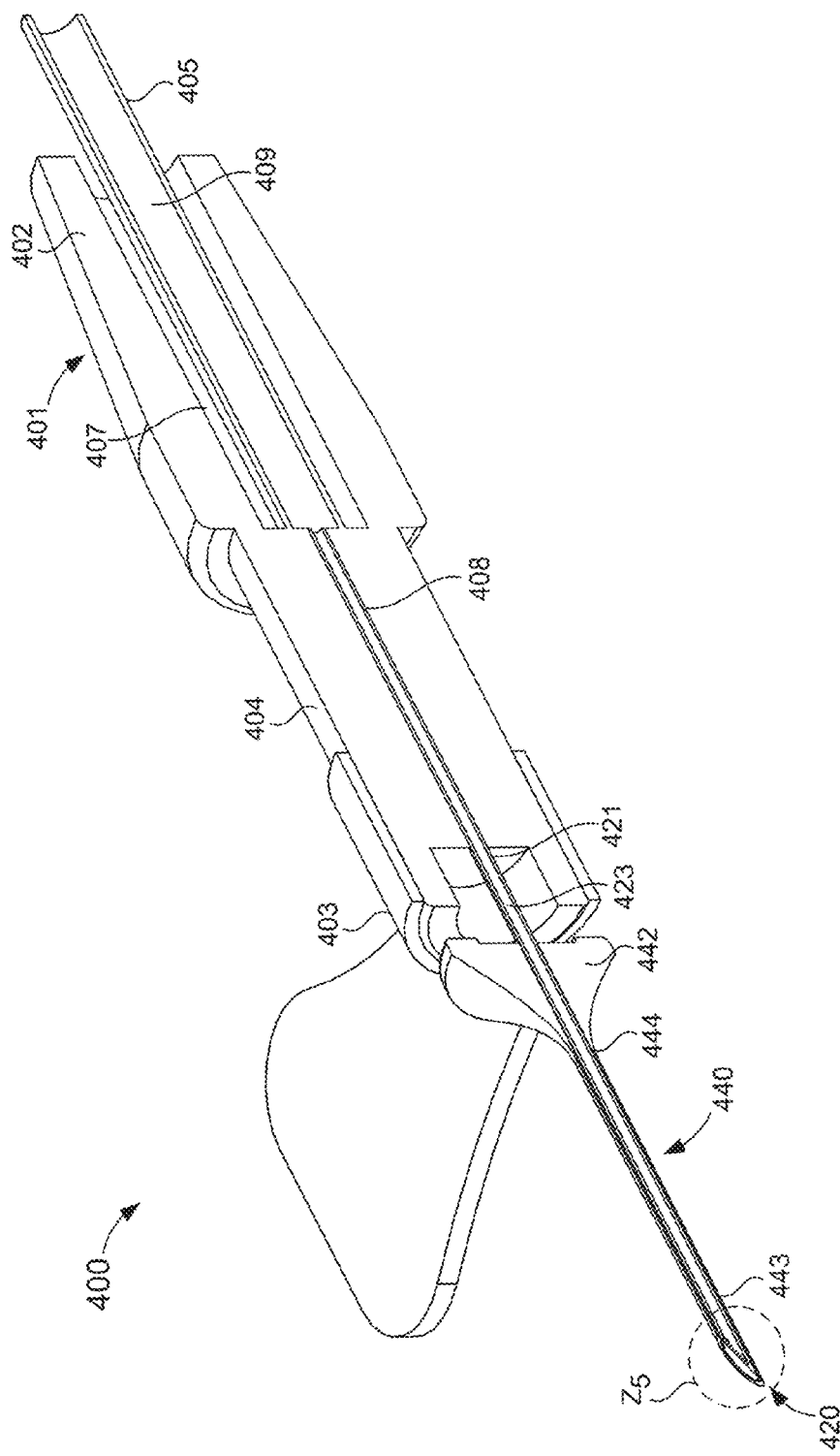
FIG. 14 is a cross-sectional view of the fluid transfer device of FIG. 13 taken along the like $X_3$-$X_3$, while in a first configuration.

The housing 401 has a proximal end portion 402, the distal end portion 403, and a medial portion 404. As shown in FIG. 13, the housing 401 can have an overall shape that is substantially similar to the housing 201 shown and described with reference to FIG. 3. The distal end portion 403 of the housing 401 can be physically and fluidically coupled to a proximal end portion 421 of the needle 420, as described above. The proximal end portion 402 can be coupled to a cannula 405. For example, as shown in FIG. 14, a portion of the cannula 405 can be disposed within an opening 407 defined by the proximal end portion 402 of the housing 401. When disposed within the opening 407, the cannula 405 can be physically and fluidically coupled to the medial portion 404 of the housing 401, as described above with reference to FIGS. 3-5. Therefore, a lumen 409 defined by the cannula 405 is placed in fluid communication with a fluid flow path 408 defined by the medial portion 404 of the housing 401.

Figure 15:
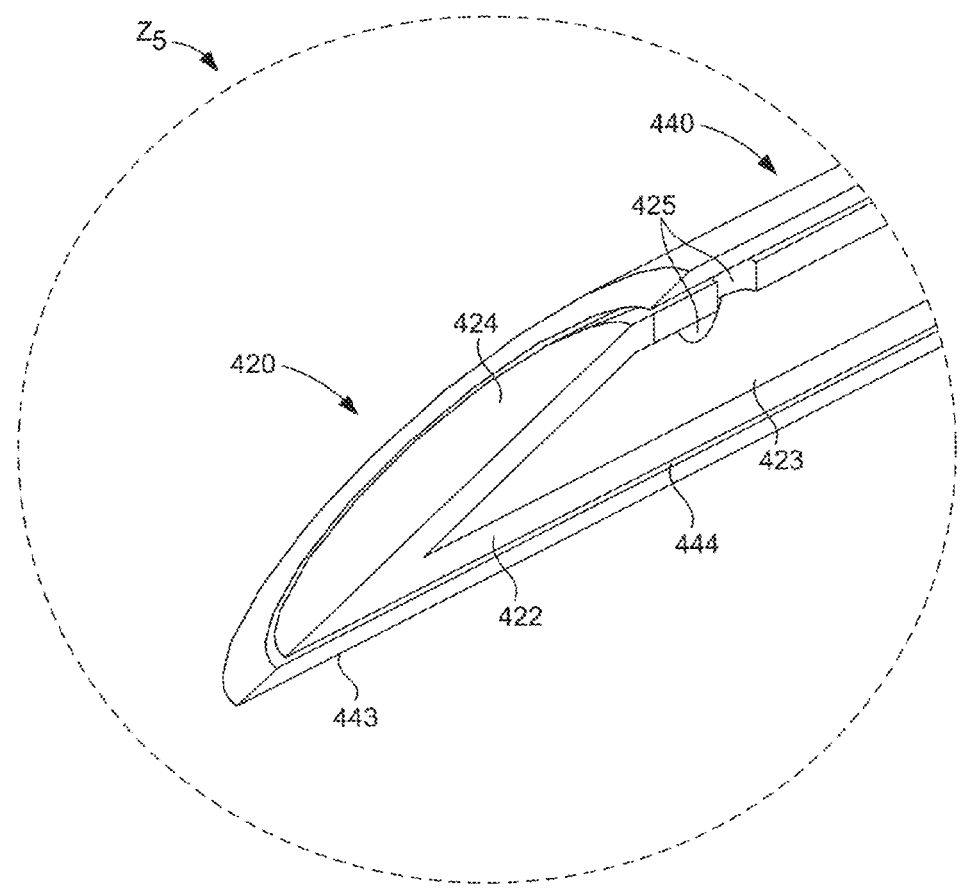
FIG. 15 is an enlarged view of a portion of the fluid transfer device of FIG. 13 in the first configuration and identified in FIG. 14 as region $Z_5$.
Figure 16:
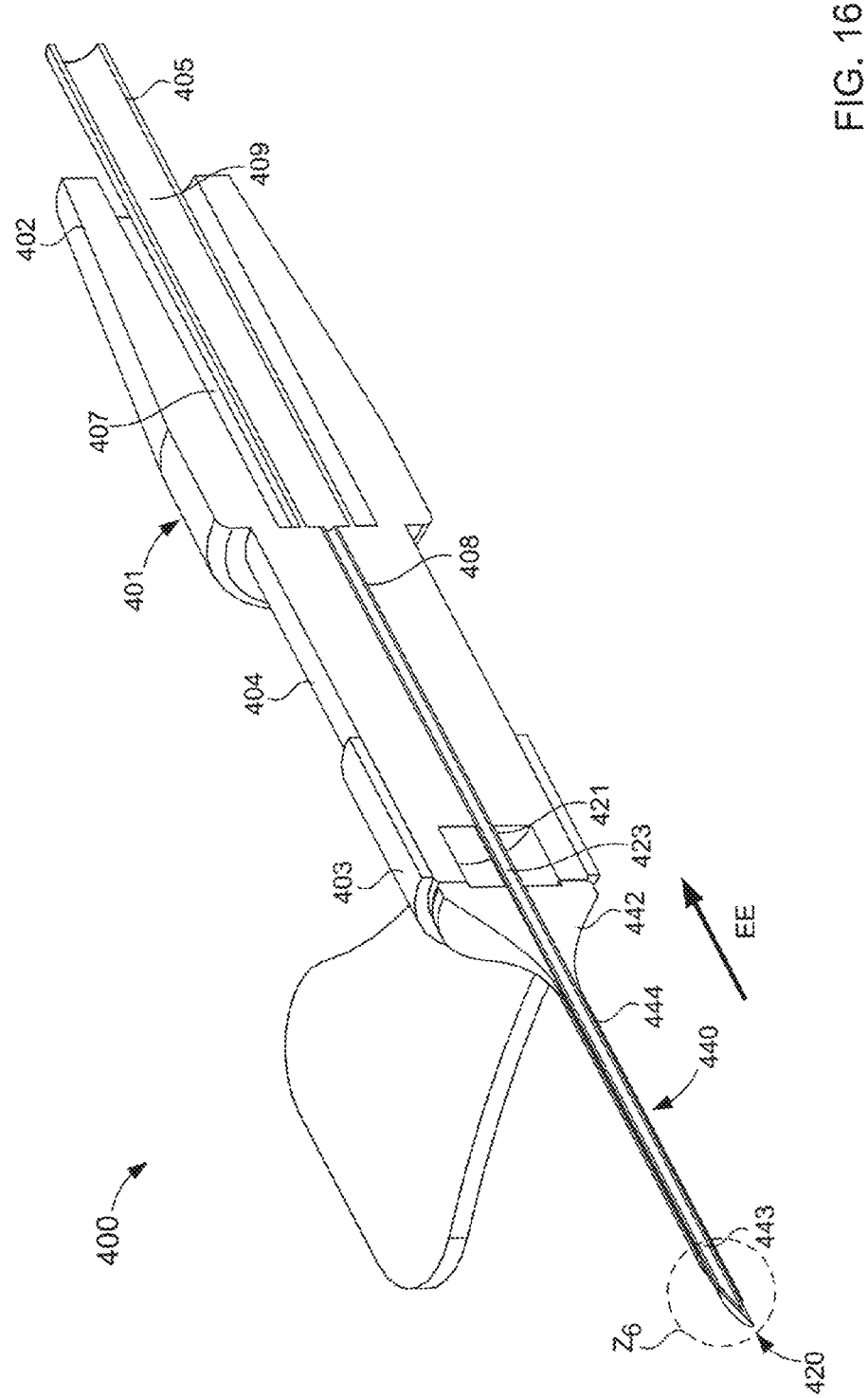
FIG. 16 is a cross-sectional view of the fluid transfer device of FIG. 13 taken along the line $X_3$-$X_3$, while in a second configuration.

The occlusion mechanism 440 has a proximal end portion 442 and a distal end portion 443, and defines a lumen 444 therebetween. The occlusion mechanism 440 is disposed about a portion of the needle 420 and can be movable between a first configuration (FIG. 14) and a second configuration (FIG. 16). Similarly stated, the occlusion member (mechanism) 440 is movably disposed about the needle 420 such that at least a portion of the needle 420 is disposed within the lumen 444 of the occlusion member 440. As shown in FIGS. 14 and 15, when the first configuration, the distal end portion 443 of the occlusion member 440 is substantially aligned with the distal end portion 422 of the needle 420. Said another way, a distal end surface of the occlusion member 440 can be substantially parallel and aligned (e.g., coplanar) with a distal end surface of the needle 420, when the occlusion member 440 is in the first configuration.

The arrangement of the occlusion member 440 can be such that an outer surface of the needle 420 is in contact with an inner surface of the occlusion member 440 that defines the lumen 444. In this manner, the inner surface of the occlusion member 440 and the outer surface of the needle 420 can form a friction fit (e.g., a similar arrangement to the needle 220 and the occlusion member 221 shown in described above with reference to FIGS. 3-5). As shown in FIG. 15, when the distal end portion 443 of the occlusion member 440 is aligned with the distal end portion 422 of the needle 420, the openings 425 of the needle 420 are disposed within the lumen 444 of the occlusion member 440. Therefore, the lumen 423 of the needle 420 is substantially fluidically isolated from a volume outside of the needle 420 (e.g., a volume disposed proximally relative to the needle 420). In other words, the openings 425 and the lumen 423 of the needle 420 are obstructed by the occlusion member 440.

In use, the transfer device 400 can be in the first configuration (FIG. 14) and a proximal end portion of the cannula 405 can be physically and fluidically coupled to a fluid reservoir (not shown). The fluid reservoir can be any suitable fluid reservoir such as, for example, those described above with reference to the fluid reservoir 130 of FIGS. 1 and 2. With the cannula 405 coupled to the fluid reservoir and with the transfer device 400 in the first configuration, a user (e.g., a physician, a nurse, a technician, a phlebotomist, or the like) can manipulate the transfer device 400 to insert the needle 420 into a patient. In this manner, the distal end portion 422 of the needle 420 can pierce the skin of the patient to dispose the distal end portion 422 of the needle 420 within, for example, a vein. In some instances, the venipuncture event (e.g., the insertion of the distal end portion 422 of the needle 420 into the vein) can dislodge, for example, dermally residing microbes from the insertion point. Thus, with the needle 420 having the closed tip 424 (FIG. 15) and with the occlusion member 440 obstructing the openings 425, the lumen 423 of the needle 420 is isolated from the dislodged dermally residing microbes and/or other undesirable external contaminants.

Figure 17:
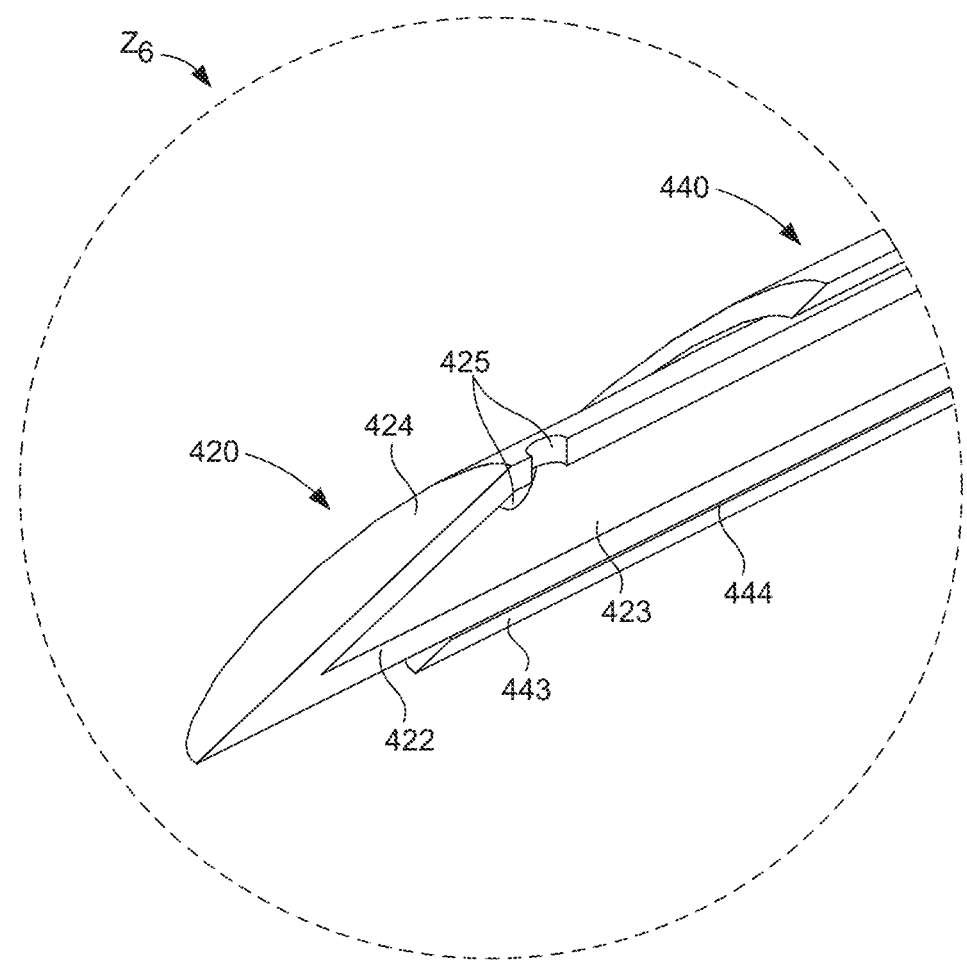
FIG. 17 is an enlarged view of a portion of the fluid transfer device of FIG. 13 in the second configuration and identified in FIG. 16 as region $Z_6$.

Once the distal end portion 422 of the needle 420 is disposed within the vein, the occlusion member 440 can be moved to the second configuration to place the transfer device 400 in the second configuration, as indicated by the arrow EE in FIG. 16. For example, the user can slide the occlusion member 440 along the length of the needle 420 in the EE direction (i.e., the proximal direction) such that the proximal end portion 442 of the occlusion member 440 is in contact with the distal end portion 403 of the housing 401. In this manner, the distal end portion 443 of the occlusion member 440 can be moved to a distal position relative to the openings 425 of the needle 420, as shown in FIG. 17. Thus, the openings 425 of the needle 420 are substantially unobstructed and can place the lumen 423 in fluid communication with the vein in which the needle 420 is disposed. Therefore, the movement of the occlusion member 440 to the second configuration places the fluid reservoir (not shown) in fluid communication with the vein of the patient via the openings 425 and lumen 423 of the needle 420, the fluid flow path 408 of the housing 401, and the lumen 409 of the cannula 405. Said another way, the openings 425 of the needle 420 are substantially unobstructed such that a flow of fluid substantially free from contaminates (e.g., dermally residing microbes) can be transferred to or from the patient via the openings 425 and the lumen 423 of the needle 420, the fluid flow path 408 of the housing 401, and the lumen 409 of the cannula 405.

While the distal end portion 443 of occlusion member 440 is shown and described in FIGS. 13-17 as beings substantially aligned (e.g., coplanar) with the distal end portion 422 of the needle 420, in other embodiments, the distal end portion 443 of the occlusion member 440 can be offset from the distal tip 424 of the needle 420. For example, in some embodiments, a needle can include a distal tip having a diameter that is larger than a diameter of the remaining portion of the needle. In such embodiments, an occlusion member can define a lumen with an inner diameter that substantially corresponds to the diameter of the remaining portion of the needle (e.g., other than the distal tip) and the occlusion member can have an outer diameter that substantially corresponds to the diameter of the distal tip of the needle. Thus, when in a first configuration, the occlusion member can be disposed adjacent to the distal tip such that a substantially smooth transition from the diameter of the distal tip to the outer diameter of the occlusion member is formed. In some embodiments, the change in diameter from the distal tip to the remaining portion of the needle forms a shoulder that can be any substantially liner and arranged at any given angle. In other embodiments, the shoulder can be substantially nonlinear. Moreover, the arrangement of the distal surface of the occlusion member can be such that the distal surface of the occlusion member matingly couples to the shoulder of the needle.

Although not shown in FIGS. 13-17, in some embodiments, the transfer device 400 and/or a portion thereof can be included in any suitable transfer device or system that is configured to withdraw a sample of bodily fluid from and/or parenterally deliver a fluid to a patient, which is substantially free of contamination from, for example, dermally residing microbes, undesirable bodily tissue, and/or the like. For example, in some embodiments, the transfer device 100 and/or portion thereof can be included in any of the transfer devices described above with reference to the transfer device 400 in FIGS. 1 and 2.

Although the occlusion member 440 is shown and described in FIGS. 13-17 as being translated (slid) along a length of the needle 420 from the first configuration to the second configuration, in other embodiments, a transfer device can include an occlusion mechanism (occlusion member) that is rotated relative to the needle to move from a first configuration to a second configuration. For example, FIGS. 18-22 illustrate a fluid transfer device 500 (also referred to herein as "transfer device" according to an embodiment). The transfer device 500 includes a housing 501, a needle 520, and an occlusion mechanism 540 (also referred to herein as "occlusion member"). The needle 520 has a proximal end portion 521 and a distal end portion 522 and defines a lumen 523 therebetween. The proximal end portion 521 of the needle 520 is physically and fluidically coupled to a distal end portion 503 of the housing 501, as described above with reference to FIGS. 1 and 2. The distal end portion 522 of the needle 520 defines a set of openings 525 disposed along a circumference of the needle 520 that place the lumen 523 of the needle 520 in fluid communication with a volume outside of the needle 520. More specifically, the distal end portion 522 of the needle 520 has a solid (i.e., closed) tip 524 (see e.g., FIG. 20) that obstructs the distal end of the needle 520. Thus, the needle 520 can be substantially similar to the needle 520 shown and described above with reference to FIGS. 13-17. In this manner, the needle 520 can be inserted into a patient such that a fluid can be transfer to or from the patient via the openings 525 and the lumen 523 of the needle 520, as described in further detail herein.

Figure 18:
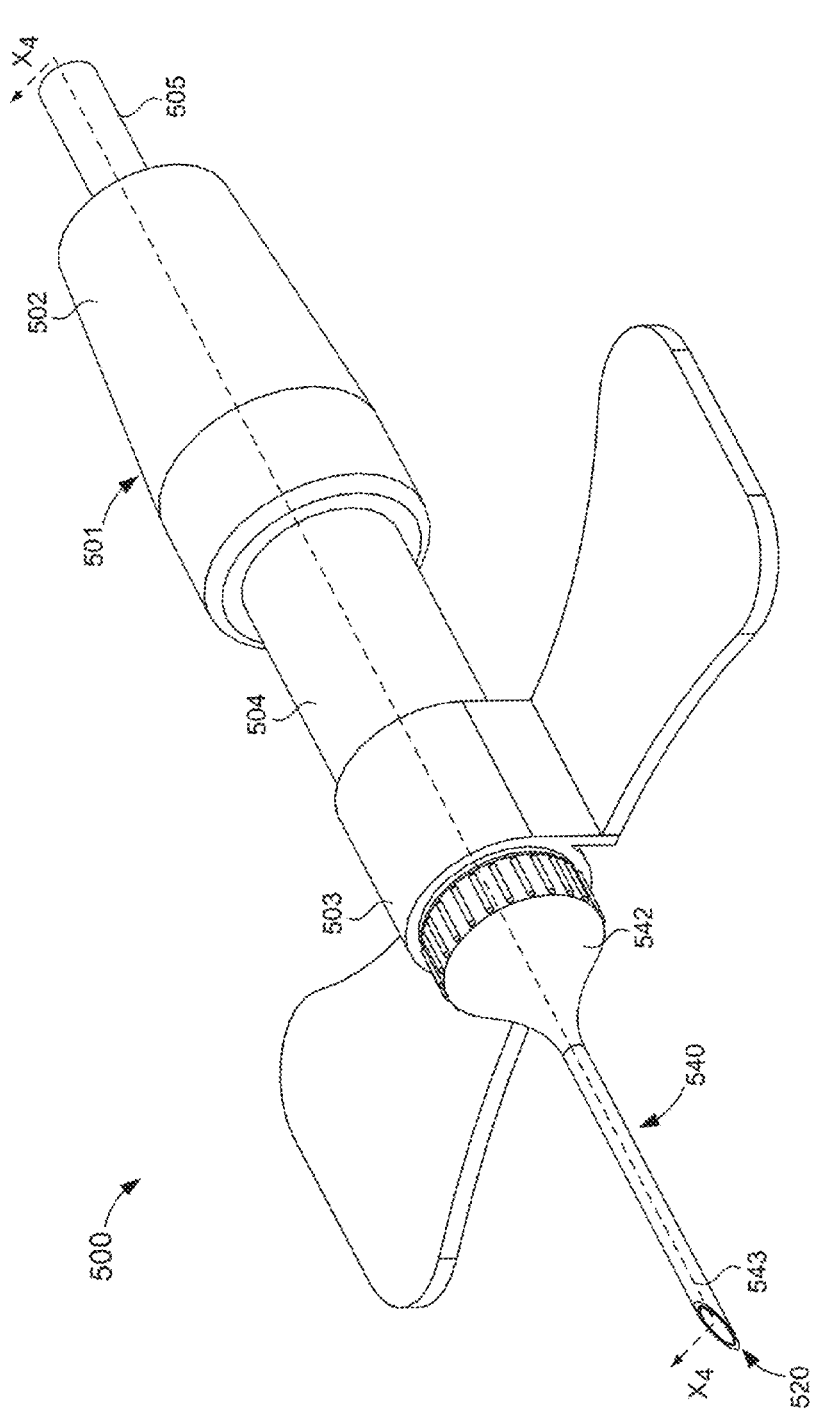
FIG. 18 is a perspective view of a fluid transfer device in according to an embodiment.
Figure 19:
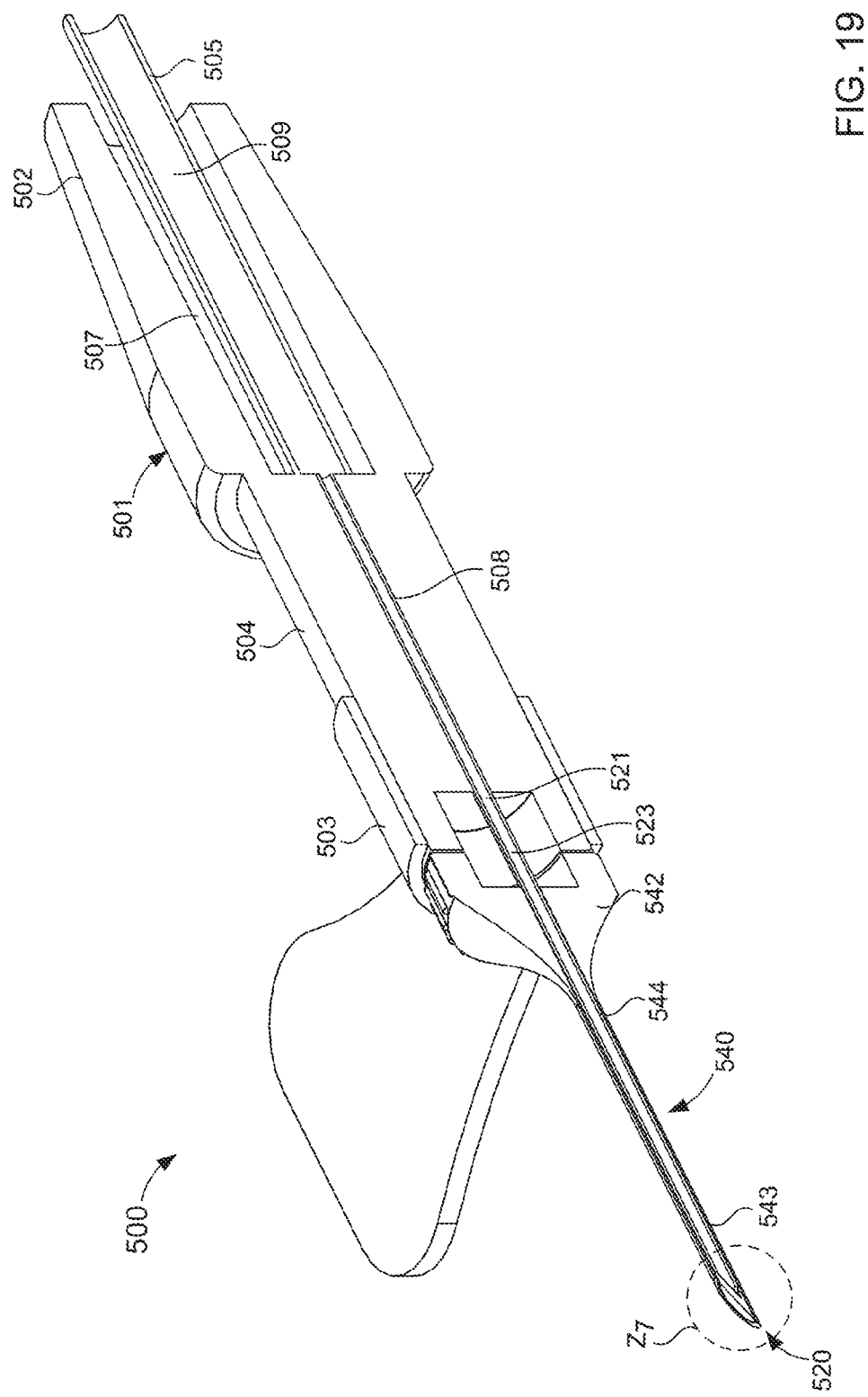
FIG. 19 is a cross-sectional view of the fluid transfer device of FIG. 18 taken along the like $X_4$-$X_4$, while in a first configuration.

The housing 501 has a proximal end portion 502, the distal end portion 503, and a medial portion 504. As shown in FIG. 18, the housing 501 can have an overall shape that is substantially similar to the housing 201 shown and described with reference to FIG. 3. The distal end portion 503 of the housing 501 can be physically and fluidically coupled to a proximal end portion 521 of the needle 520, as described above. The proximal end portion 502 can be coupled to a cannula 505. For example, as shown in FIG. 19, a portion of the cannula 505 can be disposed within an opening 507 defined by the proximal end portion 502 of the housing 501. When disposed within the opening 507, the cannula 505 can be physically and fluidically coupled to the medial portion 504 of the housing 501, as described above with reference to FIGS. 3-5. Therefore, a lumen 509 defined by the cannula 505 is placed in fluid communication with a fluid flow path 508 defined by the medial portion 504 of the housing 501.

Figure 20:
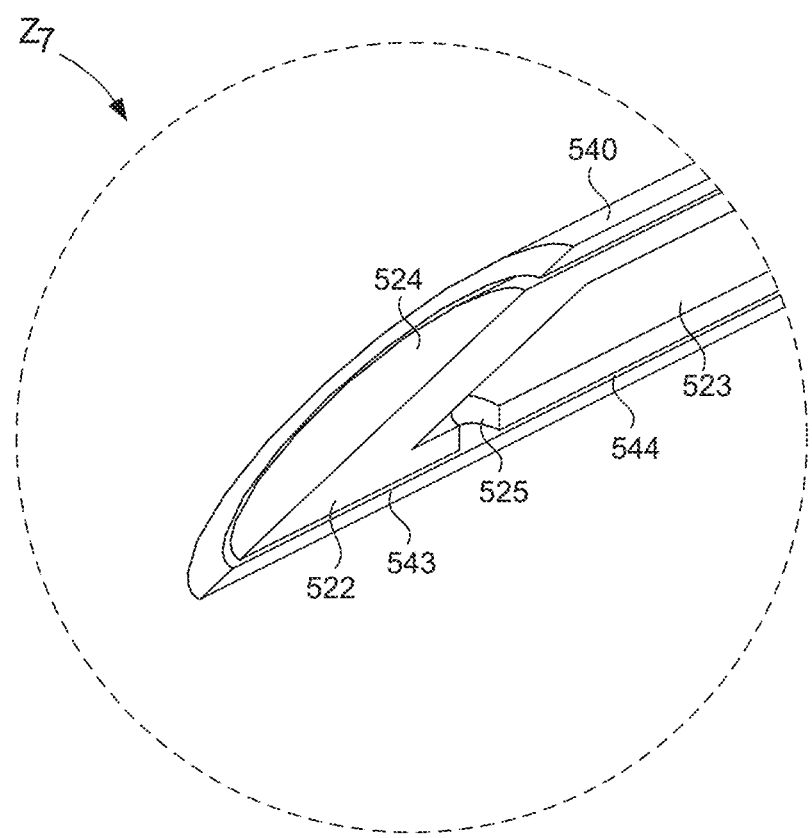
FIG. 20 is an enlarged view of a portion of the fluid transfer device of FIG. 18 in the first configuration and identified in FIG. 19 as region $Z_7$.
Figure 21:
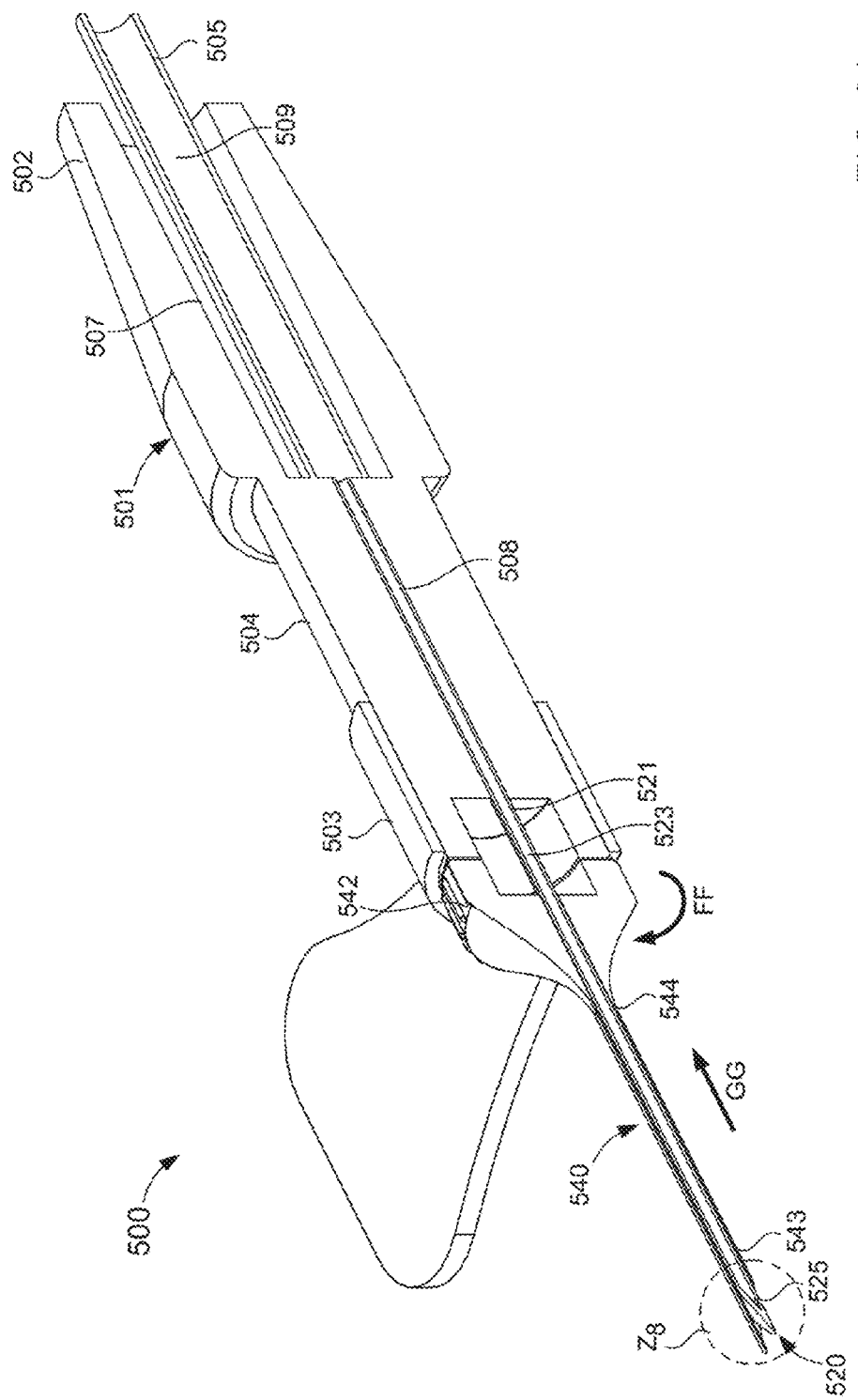
FIG. 21 is a cross-sectional view of the fluid transfer device of FIG. 18 taken along the line $X_4$-$X_4$, while in a second configuration.

The occlusion mechanism 540 has a proximal end portion 542 and a distal end portion 543, and defines a lumen 544 therebetween. The proximal end portion 542 of the occlusion member 540 is disposed adjacent to the distal end portion 503 of the housing 501. The occlusion mechanism 540 is disposed about a portion of the needle 520 and can be movable between a first configuration (FIG. 19) and a second configuration (FIG. 21). Similarly stated, the occlusion member (mechanism) 540 is movably disposed about the needle 520 such that at least a portion of the needle 520 is disposed within the lumen 544 of the occlusion member 540. As shown in FIGS. 19 and 20, when the first configuration, the distal end portion 543 of the occlusion member 540 is substantially aligned with the distal end portion 522 of the needle 520 and is arranged relative to the needle 520 to obstruct the openings 525. Further, the arrangement of the occlusion member 540 can be such that an outer surface of the needle 520 is in contact with an inner surface of the occlusion member 540 that defines the lumen 544. In this manner, the inner surface of the occlusion member 540 and the outer surface of the needle 520 can form a friction fit, as described above with reference to FIGS. 13-17. Therefore, the lumen 523 of the needle 520 is substantially fluidically isolated from a volume outside of the needle 520 (e.g., a volume disposed proximally relative to the needle 520). In other words, the openings 525 and the lumen 523 of the needle 520 are obstructed by the occlusion member 540.

In use, the transfer device 500 can be in the first configuration (FIG. 19) and a proximal end portion of the cannula 505 can be physically and fluidically coupled to a fluid reservoir (not shown). The fluid reservoir can be any suitable fluid reservoir such as, for example, those described above with reference to the fluid reservoir 130 of FIGS. 1 and 2. With the cannula 505 coupled to the fluid reservoir and with the transfer device 500 in the first configuration, a user (e.g., a physician, a nurse, a technician, a phlebotomist, or the like) can manipulate the transfer device 500 to insert the needle 520 into a patient. In this manner, the distal end portion 522 of the needle 520 can pierce the skin of the patient to dispose the distal end portion 522 of the needle 520 within, fir example, a vein. In some instances, the venipuncture event (e.g., the insertion of the distal end portion 522 of the needle 520 into the vein) can dislodge, for example, dermally residing microbes from the insertion point. Thus, with the needle 520 having the closed tip 524 (FIG. 20) and with the occlusion member 540 obstructing the openings 525, the lumen 523 of the needle 520 is isolated from the dislodged dermally residing microbes.

Once the distal end portion 522 of the needle 520 is disposed within the vein, the occlusion member 540 can be moved from the first configuration to the second configuration to place the transfer device 500 in the second configuration, as indicated by the arrow FE in FIG. 21. For example, the user can rotate the occlusion member 540 in the FF direction such that the distal end portion 543 of the occlusion member 540 is rotated relative to the distal end portion 522 of the needle 520. Expanding further, the distal end portion 522 of the needle 520 and the distal end portion 543 of the occlusion member 540 each include an angles surface (e.g., a sharpened tip). Thus, the rotation of the occlusion member 540 misaligns the distal surfaces of the needle 520 and the occlusion member 540. In this manner, the occlusion member 540 can be rotated to expose the openings 525 of the needle 520 such that the openings 525 are substantially unobstructed as shown in FIG. 22), thereby placing the lumen 523 in fluid communication with the vein in which the needle 520 is disposed.

The movement of the occlusion member 540 to the second configuration places the fluid reservoir (not shown) in fluid communication with the vein of the patient via the openings 525 and lumen 523 of the needle 520, the fluid flow path 508 of the housing 501, and the lumen 509 of the cannula 505. Said another way, the openings 525 of the needle 520 are substantially unobstructed such that a flow of fluid substantially free from contaminates (e.g., dermally residing microbes) can be transferred to or from the patient via the openings 525 and the lumen 523 of the needle 520, the fluid flow path 508 of the housing 501, and the lumen 509 of the cannula 505, as indicated by the arrow GG in FIG. 21.

Figure 22:
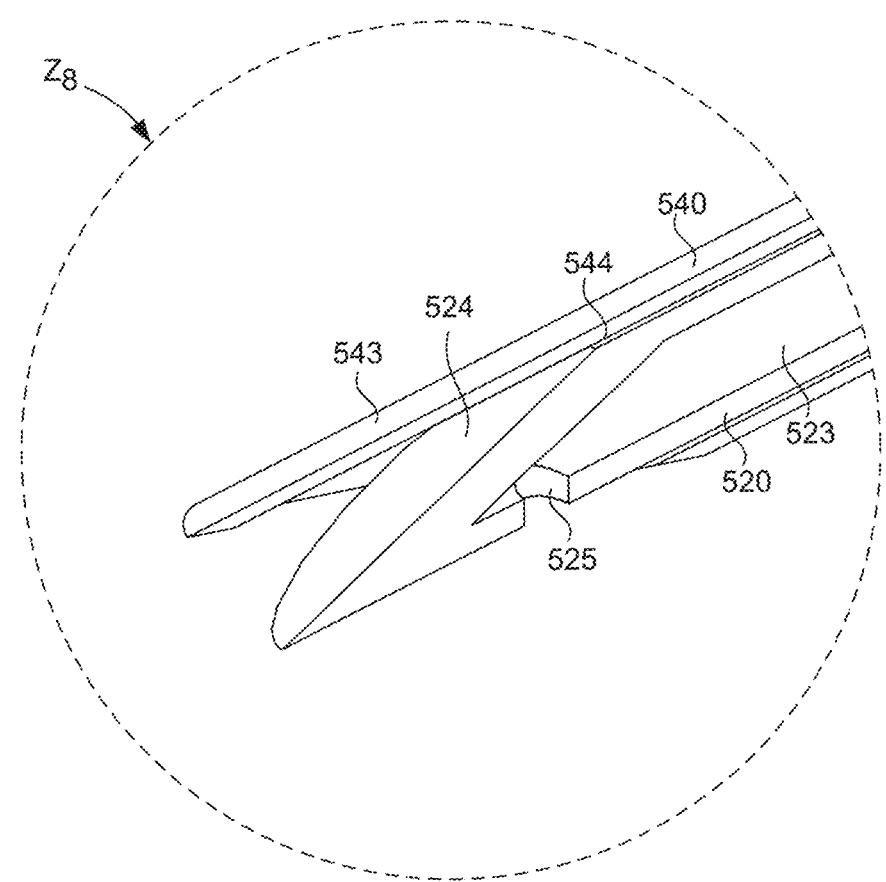
FIG. 22 is an enlarged view of a portion of the fluid transfer device of FIG. 18 in the second configuration and identified in FIG. 21 as region $Z_8$.

While the needle 520 is shown in FIG. 22 as including a single opening 525 disposed on the circumference of the needle 520, in other embodiments, the needle 525 can define any suitable number of openings 525 in any suitable arrangement. For example, in some embodiments, the needle 520 can define more than one opening 525 along the circumference of the needle 520 (e.g., perpendicular to the length of the needle 520). In other embodiments, the more than one opening 525 can be linearly arranged along a length of the needle 520 (e.g., adjacent to the existing opening 525 shown in FIG. 22). Thus, when the occlusion member 540 is rotated relative to the needle 520 the linearly aligned openings 525 can be substantially unobstructed. In still other embodiments, the openings 525 can be disposed in a non-linear arrangement.

Although not shown in FIGS. 18-22, in some embodiments, the transfer device 500 and/or a portion thereof can be included in any suitable transfer device or system that is configured to withdraw a sample of bodily fluid from and/or parenterally deliver a fluid to a patient, which is substantially free of contamination from, for example, dermally residing microbes, undesirable bodily tissue, and/or the like. For example, in some embodiments, the transfer device 500 and/or portion thereof can be included in any of the transfer devices described above with reference to the transfer device 100 in FIGS. 1 and 2.

While the distal surface of the occlusion member 540 is shown and described as being aligned (e.g., coplanar) with the distal surface of the needle 520 when the occlusion member 540 is in the first configuration, in other embodiments, a transfer device can include an occlusion member that at least temporarily circumscribes substantially the entire needle. For example, FIGS. 23-27 illustrate a fluid transfer device 600 (also referred to herein as "transfer device") according to an embodiment. The transfer device 600 includes a housing 601, a needle 620, and an occlusion mechanism 640 (also referred to herein as "occlusion member"). The needle 620 has a proximal end portion 621 and a distal end portion 622 and defines a lumen 623 therebetween. The proximal end portion 621 of the needle 620 is physically and fluidically coupled to a distal end portion 603 of the housing 601, as described above with reference to FIGS. 1 and 2. The distal end portion 622 of the needle 620 defines a set of openings 625 disposed along a circumference of the needle 620 that place the lumen 623 of the needle 620 in fluid communication with a volume outside of the needle 620. The distal end portion 622 also defines a recessed portion 626 that can be configured to retain at least a portion of skin that can be dislodged during a venipuncture event. In this manner, the needle 620 can be inserted into a patient such that a fluid can be transferred to or from the patient via the openings 625 and the lumen 623 of the needle 620, as described in further detail herein.

Figure 23:
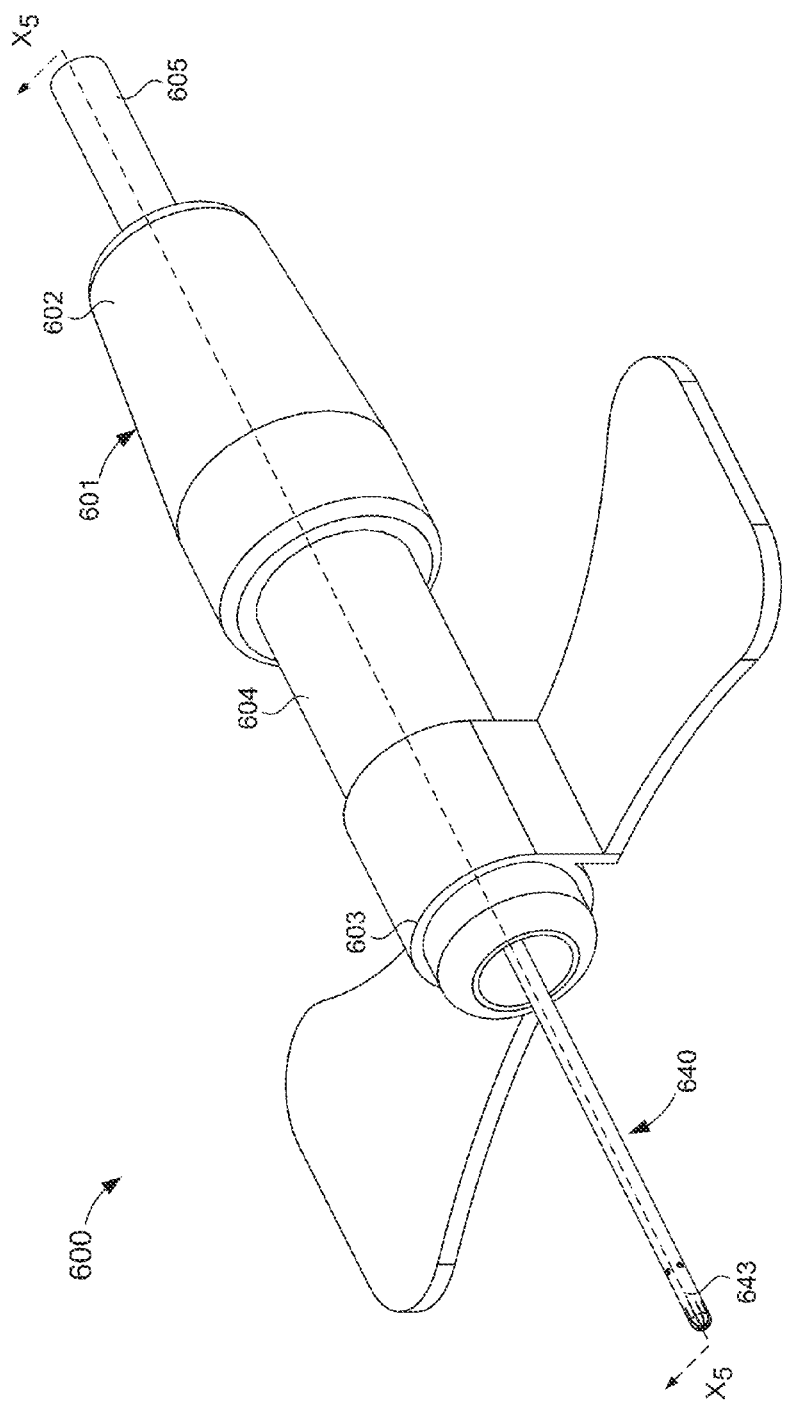
FIG. 23 is a perspective view of a fluid transfer device in according to an embodiment.
Figure 24:
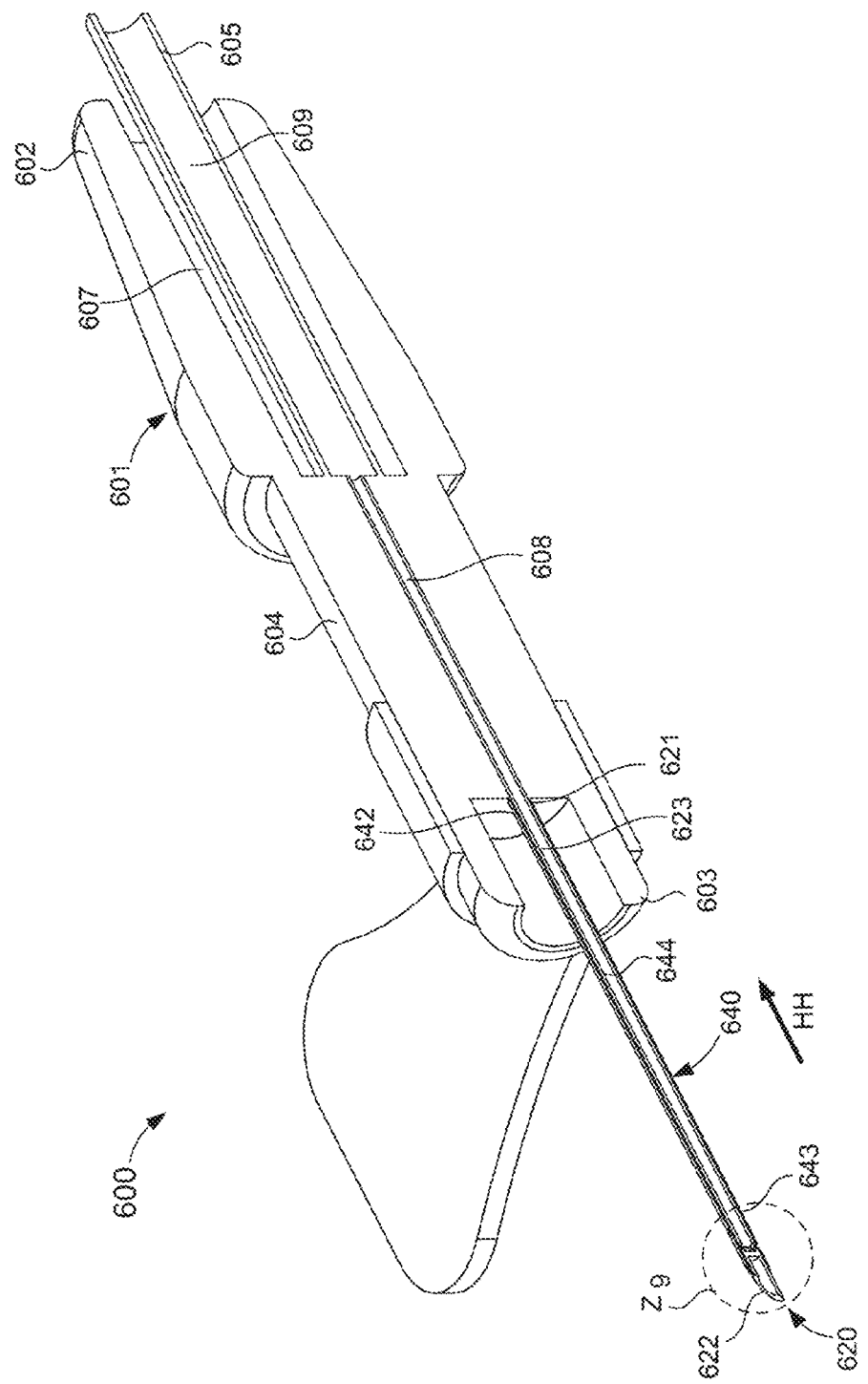
FIG. 24 is a cross-sectional view of the fluid transfer device of FIG. 23 taken along the like $X_5$-$X_5$, while in a first configuration.

The housing 601 has a proximal end portion 602, the distal end portion 603, and a medial portion 604. As shown in FIG. 23, the housing 601 can have an overall shape that is substantially similar to the housing 201 shown and described with reference to FIG. 3. The distal end portion 603 of the housing 601 can be physically and fluidically coupled to a proximal end portion 621 of the needle 620, as described above. The proximal end portion 602 can be coupled to a cannula 605. For example, as shown in FIG. 24, a portion of the cannula 605 can be disposed within an opening 607 defined by the proximal end portion 602 of the housing 601. When disposed within the opening 607, the cannula 605 can be physically and fluidically coupled to the medial portion 604 of the housing 601, as described above with reference to FIGS. 3-5. Therefore, a lumen 609 defined by the cannula 605 is placed in fluid communication with a fluid flow path 608 defined by the medial portion 604 of the housing 601.

Figure 26:
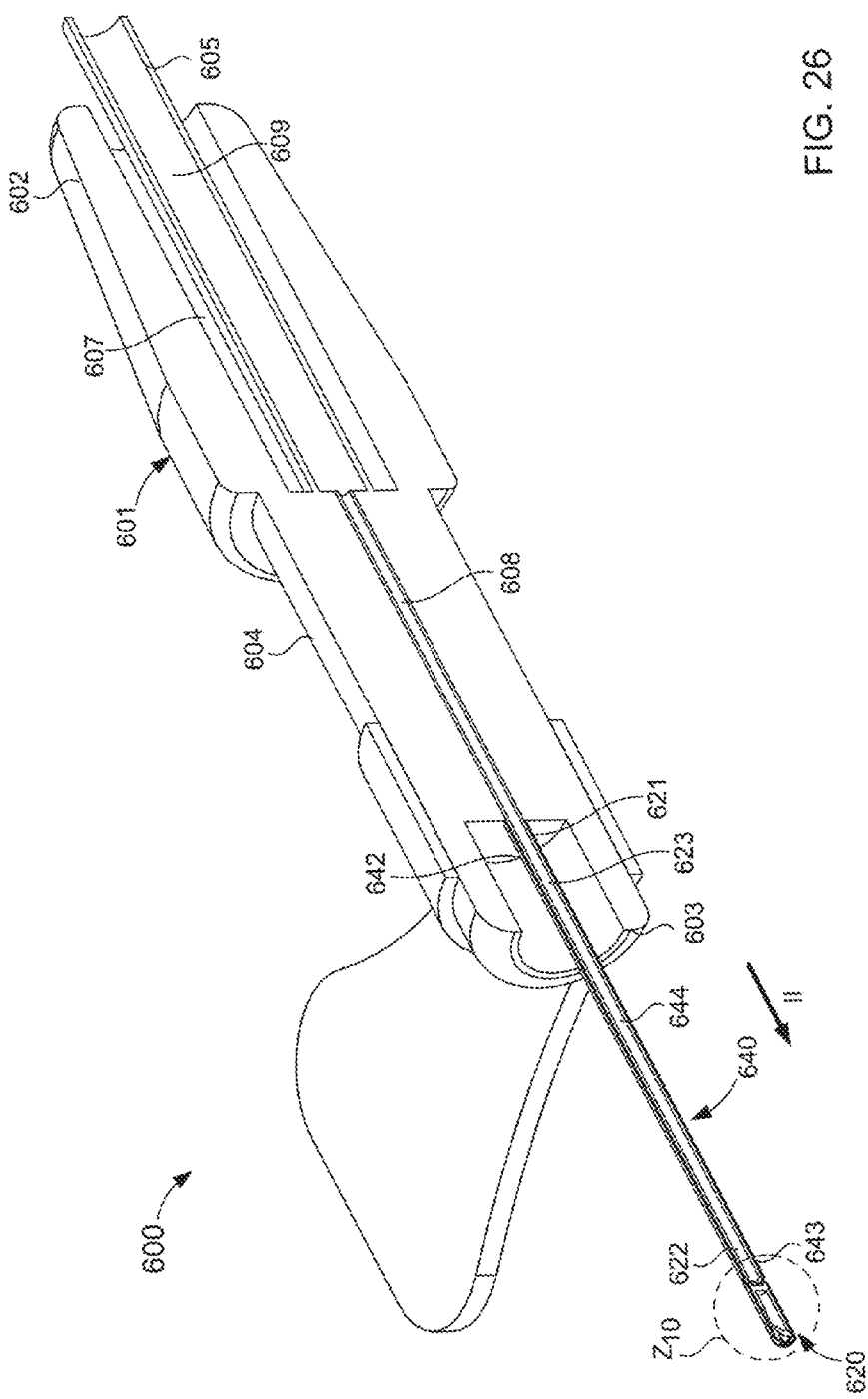
FIG. 26 is a cross-sectional view of the fluid transfer device of FIG. 23 taken along the line $X_5$-$X_5$, while in a second configuration.
Figure 27:
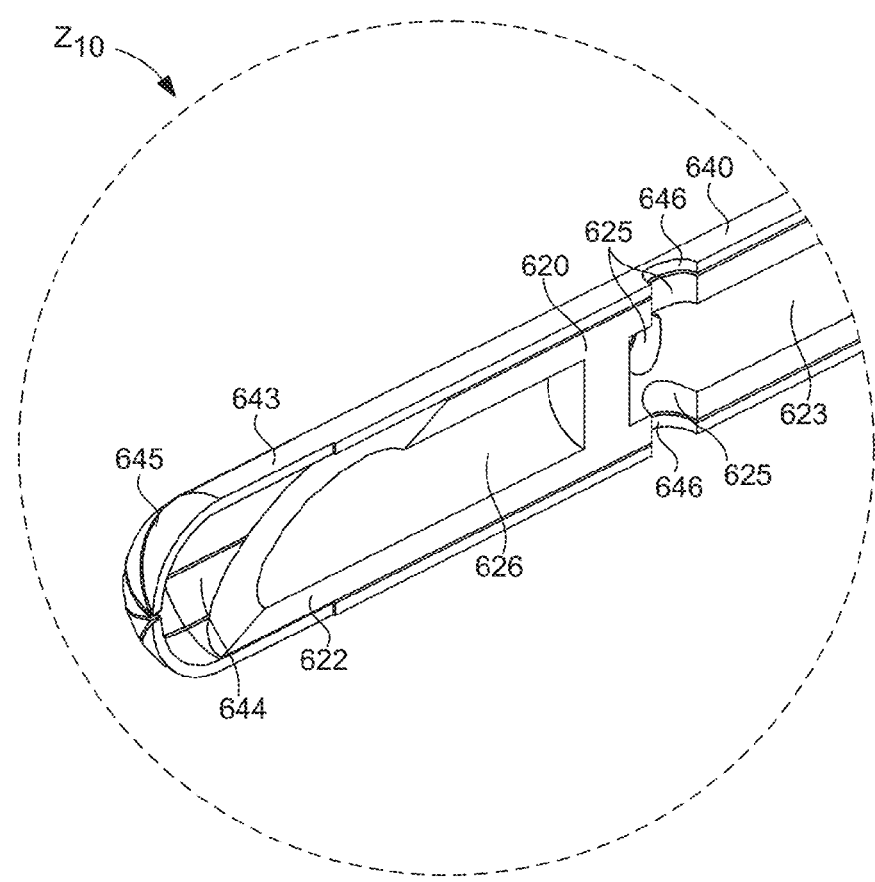
FIG. 27 is an enlarged view of a portion of the fluid transfer device of FIG. 23 in the second configuration and identified in FIG. 26 as region $Z_{10}$.

The occlusion mechanism 640 has a proximal end portion 642 and a distal end portion 643, and defines a lumen 644 therebetween. The proximal end portion 642 of the occlusion member 640 can be coupled to the medial portion 604 of the housing 601. The distal end portion 643 of the occlusion member 640 includes a set of fingers 645 that can selectively enclose the distal end portion 622 of the needle 620. As described in further detail herein, the distal end portion 643 defines a set of openings 646 that can be selectively aligned with the openings 625 of the needle 620. In this manner, the occlusion mechanism 640 is disposed about a portion of the needle 620 and can be movable between a first configuration (FIG. 23), a second configuration (FIGS. 24 and 25), and a third configuration (FIGS. 26 and 27). Similarly stated, the occlusion member (mechanism) 640 is movably disposed about the needle 620 such that the needle 620 is at least temporarily disposed within the lumen 644 of the occlusion member 640.

As shown in FIG. 23, when in the first configuration, the fingers 645 of the occlusion member 640 enclose the distal end portion 622 of the needle 620. In use, the proximal end portion of the cannula 605 can be physically and fluidically coupled to a fluid reservoir (not shown). The fluid reservoir can be any suitable fluid reservoir such as, for example, those described above with reference to the fluid reservoir 130 of FIGS. 1 and 2. With the cannula 605 coupled to the fluid reservoir and with the transfer device 600 in the first configuration, a user (e.g., a physician, a nurse, a technician, a phlebotomist, or the like) can manipulate the transfer device 600 to move the occlusion member 640 relative to the needle 620 (indicated by the arrow HH in FIG. 24), thereby placing the occlusion member 640 in the second configuration. For example, in some embodiments, the occlusion member 640 can be formed from a relatively flexible material that can include at least a portion that can be deformed (e.g., such as a bellows portion of the like). Thus, the distal end portion 643 of the occlusion member 640 can be moved in the proximal direction (i.e., the HH direction) relative to the distal end portion 622 of the needle 620.

Figure 25:
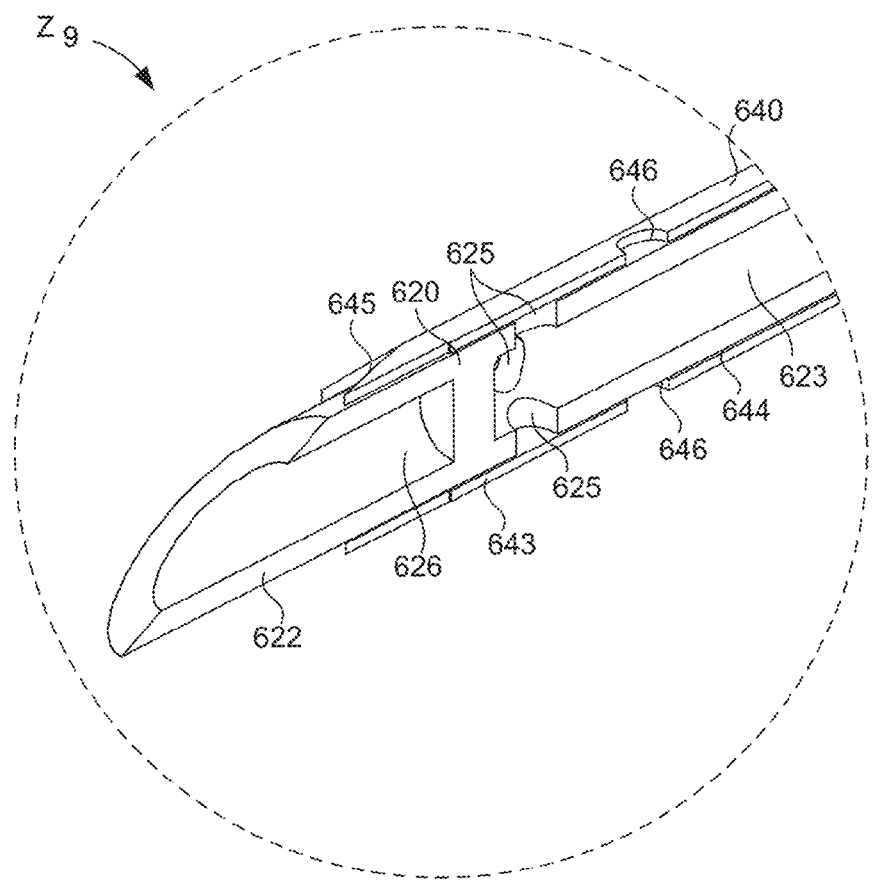
FIG. 25 is an enlarged view of a portion of the fluid transfer device of FIG. 23 in the first configuration and identified in FIG. 24 as region $Z_9$.

As shown in FIG. 25, the proximal motion of the distal end portion 643 of the occlusion member 640 is such that the fingers 645 are moved to an open configuration to expose the distal end portion 622 of the needle 620. Furthermore, the openings 646 of the occlusion member 640 are moved to a proximal position relative to the openings 625 defined by the needle 620. Therefore, the openings 625 of the needle 620 are substantially obstructed by the occlusion member 640. With the occlusion member 640 in the second configuration, the user can manipulate the transfer device 600 to insert the needle 620 into a patient. In this manner, the distal end portion 622 of the needle 620 can pierce the skin of the patient to dispose the distal end portion 622 of the needle 620 within, for example, a vein. In some instances, the venipuncture event (e.g., the insertion of the distal end portion 622 of the needle 620 into the vein) can dislodge a portion of skin that can include, for example, dermally residing microbes from the insertion point. Thus, with the distal end portion 622 of the needle 620 forming the recessed portion 626, the dislodged skin (e.g., a skin "plug") can be disposed within the recessed portion 626. Moreover, with the occlusion member 640 obstructing the openings 625, the lumen 623 of the needle 620 is isolated from the dislodged dermally residing microbes.

Once the distal end portion 622 of the needle 620 is disposed within the vein, the occlusion member 640 can be moved from the second configuration to the third configuration, as indicated by the arrow II in FIG. 26. In some embodiments, the third configuration can be substantially similar to the first configuration. For example, the distal end portion 643 of the occlusion member 640 can be moved in the distal direction (i.e., the II direction) such that the fingers 645 are again disposed about the distal end portion 622 of the needle 620. In this manner, the dislodged skin plug can be retained, by the fingers 645 of the occlusion member 640, substantially within the recessed portion 626 of the needle 620. Moreover, the openings 646 of the occlusion member 640 can again be aligned with the openings 625 of the needle 620, as shown in FIG. 27. Thus, the movement of the occlusion member 640 from the second configuration to the third configuration places the fluid reservoir (not shown) in fluid communication with the vein of the patient via the openings 646 of the occlusion member 640, openings 625 and lumen 623 of the needle 620, the fluid flow path 608 of the housing 601, and the lumen 609 of the cannula 605. Said another way, the openings 625 of the needle 620 are substantially unobstructed such that a flow of fluid substantially free from contaminates (e.g., dermally residing microbes) can be transferred to or from the patient via the openings 646 of the occlusion member 640, the openings 625 and the lumen 623 of the needle 620, the fluid flow path 608 of the housing 601, and the lumen 609 of the cannula 605.

Although not shown in FIGS. 23-27, in some embodiments, the transfer device 600 and/or a portion thereof can be included in any suitable transfer device or system that is configured to withdraw a sample of bodily fluid from and/or parenterally deliver a fluid to a patient, which is substantially free of contamination from, for example, dermally residing microbes, undesirable bodily tissue, and/or the like. For example, in some embodiments, the transfer device 600 and/or portion thereof can be included in any of the transfer devices described above with reference to the transfer device 100 in FIGS. 1 and 2.

Figure 28:
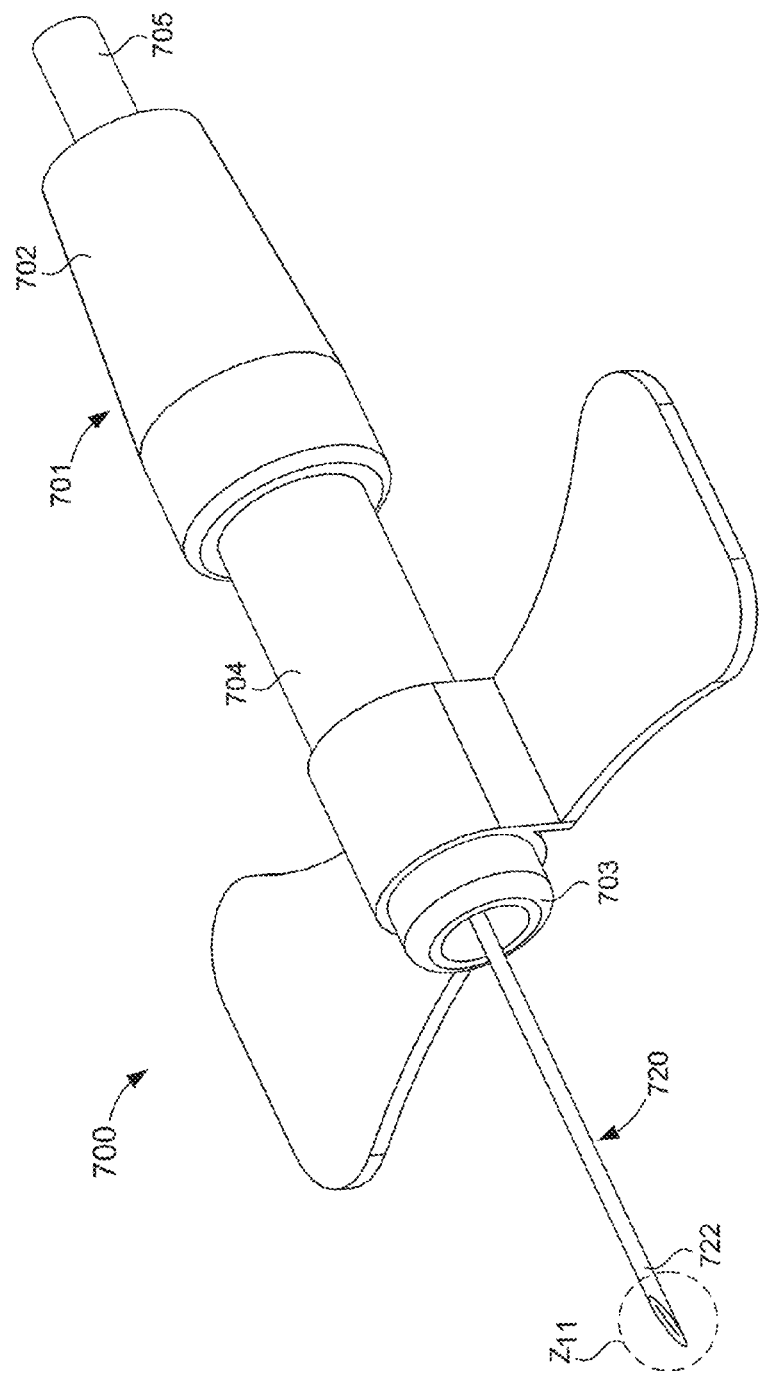
FIG. 28 is a perspective view of a fluid transfer device in according to an embodiment.
Figure 29:
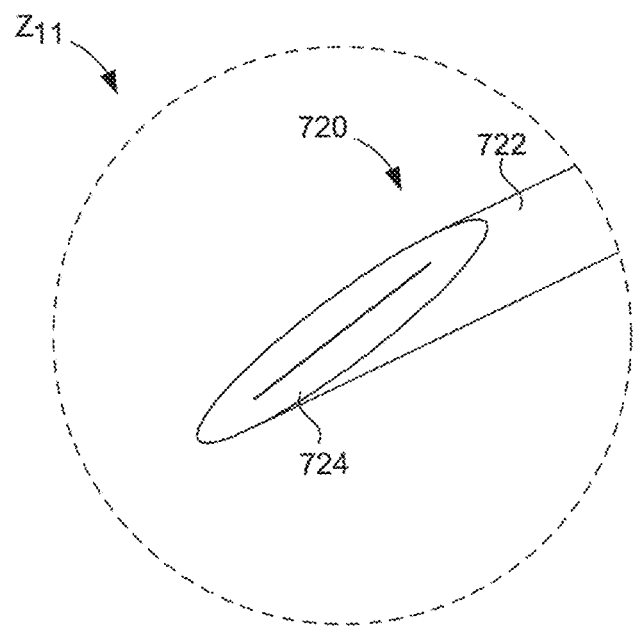
FIG. 29 is an enlarged view of a portion of the fluid transfer device of FIG. 28 in a first configuration and identified as region $Z_{11}$.
Figure 30:
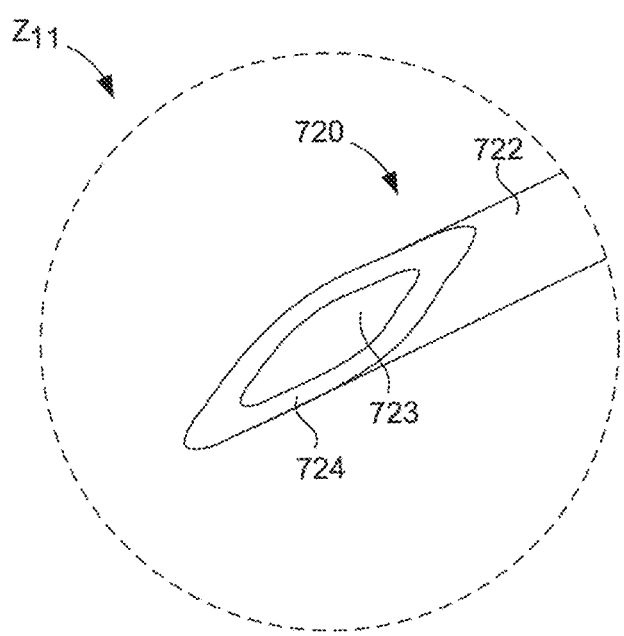
FIG. 30 is an enlarged view of the portion of the fluid transfer device of FIG. 28 in a second configuration and identified as region $Z_{11}$.

While the transfer devices 200, 300, 400, 500, and 600 described above include an occlusion member (e.g., the occlusion members 241, 341, 440, 540, and 640), in other embodiments, a transfer device can include a needle or the like that can transform between a first, obstructed configuration and a second, unobstructed configuration. For example, FIGS. 28-30 illustrate a fluid transfer device 700 (also referred to herein as "transfer device") according to an embodiment. The transfer device 700 includes a housing 701 and a needle 720. The housing 701 has a proximal end portion 702, a distal end portion 703, and a medial portion 704. As shown in FIG. 28, the housing 701 can have an overall shape that is substantially similar to the housing 201 shown and described with reference to FIG. 3. The distal end portion 703 of the housing 701 can be physically and fluidically coupled to a proximal end portion (not shown) of the needle 720, as described in further detail herein. The proximal end portion 702 can be coupled to a cannula 705. For example, a portion of the cannula 705 can be disposed within an opening (not shown) defined by the proximal end portion 702 of the housing 701. When disposed within the opening (not shown), the cannula 705 can be physically and fluidically coupled to the medial portion 704 of the housing 701, as described above with reference to FIGS. 3-5. Therefore, a lumen (not shown) defined by the cannula 705 is placed in fluid communication with a fluid flow path (not shown) defined by the medial portion 704 of the housing 701.

The needle 720 has the proximal end portion (not shown) and a distal end portion 722 and defines a lumen 723 therebetween. The proximal end portion (not shown) of the needle 720 is physically and fluidically coupled to the distal end portion 703 of the housing 701, as described above with reference to FIGS. 1 and 2. The distal end portion 722 of the needle 720 includes a distal tip 724 that can be transformable between a first configuration (FIG. 29) and a second configuration (FIG. 30). For example, in some embodiments, at least the distal end portion of the needle 720 can be formed from a shape memory alloy such as nitinol or the like in this manner, the distal tip 724 of the needle 720 can be configured to transform from the first configuration to the second configuration when exposed to a given condition such as, for example, when heated to a given temperature, when wetted, and/or the like. In this manner, when in the first configuration, the distal tip 724 of the needle 720 can be substantially closed and when placed in the given condition the distal tip 724 can transform to an open configuration (e.g., the second configuration).

In use, the transfer device 700 can be in the first configuration (FIG. 29) and a proximal end portion of the cannula 705 can be physically and fluidically coupled to a fluid reservoir (not shown). The fluid reservoir can be any suitable fluid reservoir such as, for example, those described above with reference to the fluid reservoir 130 of FIGS. 1 and 2.

With the cannula 705 coupled to the fluid reservoir and with the transfer device 700 in the first configuration, a user (e.g., a physician, a nurse, a technician, a phlebotomist, or the like) can manipulate the transfer device 700 to insert the needle 720 into a patient. In this manner, the distal end portion 722 of the needle 720 can pierce the skin of the patient to dispose the distal end portion 722 of the needle 720 within, for example, a vein. In some instances, the venipuncture event (e.g., the insertion of the distal end portion 722 of the needle 720 into the vein) can dislodge, for example, dermally residing microbes from the insertion point. Thus, with the needle 720 in the first configuration, the distal tip 724 is substantially closed (FIG. 29) such that the lumen 723 is substantially obstructed. In this manner, the lumen 723 of the needle 720 is isolated from the dislodged dermally residing microbes when the needle 720 is inserted into the patient. Once the distal end portion 722 of the needle 720 is disposed within the vein, the distal tip 724 can transform from the first configuration to the second configuration (FIG. 30). Thus, the distal tip 724 is transformed to an open configuration to place the lumen 723 in fluid communication with the vein in which the needle 720 is disposed. Moreover, the movement of the distal tip 724 to the second configuration places the fluid reservoir (not shown) in fluid communication with the vein of the patient via the lumen 723 of the needle 720, the fluid flow path (not shown) of the housing 701, and the lumen (not shown) of the cannula 705. Said another way, the lumen 723 of the needle 720 is substantially unobstructed such that a flow of fluid substantially free from contaminates (e.g., dermally residing microbes) can be transferred to or from the patient via the lumen 723 of the needle 720, the fluid flow path (not shown) of the housing 701, and the lumen (not shown) of the cannula 705.

While the needle 720 is described above as being formed from a material that can be reconfigured, in other embodiments, the needle 720 can include a coating or the like that can be transformed from the first configuration to the second configuration. For example, in some embodiments, the needle 720 can be coated with a material that can dissolve when placed in contact with a fluid (e.g., when disposed in the vein of the patient).

Although not shown in FIGS. 28-30, in some embodiments, the transfer device 700 and/or a portion thereof can be included in any suitable transfer device or system that is configured to withdraw a sample of bodily fluid from and/or parenterally deliver a fluid to a patient, which is substantially free of contamination from, for example, dermally residing microbes, undesirable bodily tissue, and/or the like. For example, in some embodiments, the transfer device 700 and/or portion thereof can be included in any of the transfer devices described above with reference to the transfer device 100 in FIGS. 1 and 2.

Figure 31:
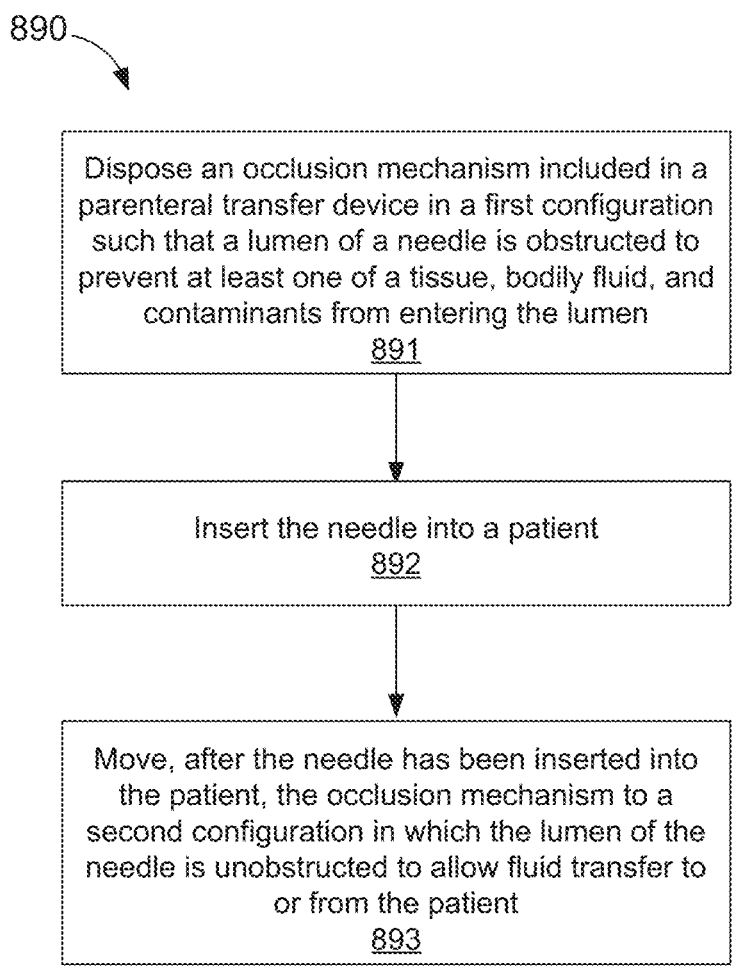
FIG. 31 is a flow chart illustrating a method of transferring a fluid to or from a patient with reduced microbial contamination and inadvertent injection of undesirable external microbes into a patient's blood stream.

FIG. 31 is a flowchart illustrating a method 890 from transferring fluid to or from a patient using a parenteral fluid transfer device, according to an embodiment. The parenteral fluid transfer device can be any suitable transfer device described herein (e.g., the transfer devices 100, 200, 300, 400, 500, 600, and/or 700). In this manner, the parenteral fluid transfer device (also referred to herein as "transfer device") includes at least a needle and an occlusion mechanism. The needle can define a lumen and is configured to be inserted into the patient. The occlusion mechanism is operable to selectively control fluid flow to or from a patient through the needle lumen.

The method 890 includes disposing the occlusion mechanism in a first configuration in which the lumen of the needle is obstructed to prevent tissue or other undesirable external contaminants from entering the lumen, at 891. For example, in some embodiments, the occlusion mechanism can include an occlusion member that is disposed within a portion of the lumen of the needle such that at least a portion of the lumen is fluidically isolated from a portion distal to the occlusion member (e.g., as described above with reference to the transfer device 200 (FIGS. 3-5) and the transfer device 300 (FIGS. 6-12)). In other embodiments, the occlusion member can be disposed about the needle and can be arranged to obstruct an opening, aperture, and/or port defined by the needle (e.g., as described above with reference to the transfer device 400 (FIGS. 13-17), the transfer device 500 (FIGS. 18-22), and/or the transfer device 600 (FIGS. 23-27). In still other embodiments, a portion of the needle can form and/or define the occlusion member (e.g., as described above with reference to the transfer device 700 (FIGS. 28-30).

While in the first configuration, the needle is inserted into the patient, at 892. In this manner, the distal end portion of the needle can pierce the skin of the patient to dispose the distal end portion of the needle within, for example, a vein. In some instances, the venipuncture event (e.g., the insertion of the distal end portion of the needle into the vein) can dislodge, for example, dermally residing microbes from the insertion point, in other instances, external contaminants and microbes may be present on a patient's skin as noted in above. Thus, with the occlusion mechanism in the first configuration where the occlusion member obstructs the lumen of the needle, the lumen is isolated from the dislodged dermally residing microbes and/or other undesirable external contaminants.

After the needle has been inserted into the patient, the occlusion mechanism is moved to a second configuration in which the lumen of the needle is unobstructed to allow fluid transfer to or from the patient, at 893. For example, the occlusion member can be translated, rotated, transformed, dissolved, and/or otherwise reconfigured from the first configuration to the second configuration. In this manner, the occlusion member can be moved relative to the needle such that the lumen is substantially unobstructed. In some embodiments, the occlusion member can be manually moved from the first configuration to the second configuration. In other embodiments, the occlusion member can automatically move or transform from the first configuration to the second configuration. In still other embodiments, the user can manipulate an actuator or the like that is operable in moving or transforming the occlusion member from the first configuration to the second configuration.

In some embodiments, the needle and/or any other suitable portion of the transfer device can be physically and fluidically coupled to a fluid reservoir (not shown). The fluid reservoir can be any suitable fluid reservoir such as, for example, known fluid reservoirs configured to collect and/or deliver a parenteral fluid. Thus, a fluid can be transferred between the patient and the fluid reservoir. In some instances, the embodiments and methods described herein can be used with a fluid transfer device such as, for example, those described in U.S. Pat. No. 8,535,241, filed Oct. 12, 2012, entitled "Fluid Diversion Mechanism for Bodily-Fluid Sampling" and U.S. Provisional Patent Application Ser. No. 61/712,468, filed Oct. 11, 2012, entitled "Systems and Methods for Delivering a Fluid to a Patient With Reduced Contamination," the disclosures of which are incorporated herein by reference in their entireties. In such instances, by obstructing the lumen of the needle as shown and described by the embodiments and methods herein, the quantity (e.g., concentration and/or volumetric ratio) of contaminants such as, for example, dermally residing microbes, included in a diversion volume is reduced. Thus, the diversion volume that is drawn prior to drawing a sample volume can be reduced. Moreover, the sample volume drawn through the lumen of the needle after the diversion volume has been collected can be substantially free from contaminants and/or the like that, in some instances, can lead to false positive or false negative results when testing the sample volume.

While various embodiments have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Additionally, certain steps may be partially completed before proceeding to subsequent steps.

While various embodiments have been particularly shown and described, various changes in form and details may be made. For example, while the occlusion member 541 is shown and described with respect to FIG. 21 as being rotated in a single direction, in other embodiments, an actuator can be rotated in a first direction (e.g., in the direction of the arrow FF in FIG. 21) and a second direction, opposite the first. In such embodiments, the rotation in the second direction can be configured to move a transfer device between the first configuration and the second configuration. In other embodiments, the rotation of the actuator in the second direction can be limited.

Although various embodiments have been described as having particular features and/or combinations of components, other embodiments are possible having any combination or sub-combination of any features and/or components from any of the embodiments described herein.

The specific configurations of the various components can also be varied. For example, the size and specific shape of the various components can be different from the embodiments shown, while still providing the functions as described herein. More specifically, the size and shape of the various components can be specifically selected for a desired rate of bodily fluid flow into a fluid reservoir or for a desired rate of parenteral fluid flow into the patient. Similarly, the size and/or specific shape of various components can be specifically selected for a desired fluid reservoir. For example, portions of the embodiments described herein can be modified such that any suitable container, microcontainer, microliter container, vial, microvial, microliter vial, nanovial, sample bottle, culture bottle, etc. can be placed in contact with a disinfection member to sterilize one or more interfaces associated therewith prior to a bodily-fluid being drawn into a volume so defined.

The invention claimed is:

1. A method for transferring fluid to or from a patient using a parenteral transfer device, the device including a housing defining a fluid flow path, a needle having a lumen in fluid communication with the fluid flow path and being configured for insertion into the patient, and an occlusion mechanism operable to selectively control fluid flow to or from a patient through the needle lumen and the fluid flow path, the occlusion mechanism includes an occlusion member disposed about at least a portion of the needle and configured to selectively obstruct the lumen of the needle during insertion into the patient, the method comprising:

disposing the occlusion member in a first position relative to the needle prior to insertion into the patient to place the occlusion mechanism in a first configuration in which the lumen of the needle is obstructed to prevent at least one of tissue, bodily fluid, and contaminants from entering the lumen;

inserting the needle into the patient, the occlusion mechanism being in the first configuration as the needle is inserted into the patient;

after the needle has been inserted into the patient, rotating the occlusion member from the first position to a second position to place the occlusion mechanism in a second configuration in which the lumen of the needle is unobstructed and the occlusion member is disposed outside of the fluid flow path; and transferring a volume of a fluid substantially free of tissue and contaminants between the patient and a fluid reservoir in fluid communication with the fluid flow path when the occlusion mechanism is in the second configuration.

2. The method of claim 1, wherein the occlusion member is manually rotated from the first position to the second position.

3. The method of claim 1, wherein the occlusion member is mechanically rotated from the first position to the second position.

4. The method of claim 1, wherein the occlusion member is automatically rotated from the first position to the second position.

5. The method of claim 1, wherein the needle includes a recessed portion fluidically isolated from the needle lumen, the recessed portion configured to receive and retain at least one of tissue, bodily fluid, and contaminants when the needle is inserted into the patient.

* * * * *